(12) United States Patent
Molina et al.

(10) Patent No.: US 11,623,096 B2
(45) Date of Patent: Apr. 11, 2023

(54) STIMULATION INDUCED NEURAL RESPONSE FOR PARAMETER SELECTION

(71) Applicant: Medtronic, Inc., Minneapolis, MN (US)

(72) Inventors: Rene A. Molina, Maple Grove, MN (US); Scott R. Stanslaski, Shoreview, MN (US); Jadin C. Jackson, Roseville, MN (US); Christopher L. Pulliam, Plymouth, MN (US); Eric J. Panken, Edina, MN (US); Michelle A. Case, Fridley, MN (US); Abbey Beuning Holt Becker, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/945,624

(22) Filed: Jul. 31, 2020

(65) Prior Publication Data
US 2022/0032063 A1    Feb. 3, 2022

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/3615* (2013.01);
(Continued)

(58) Field of Classification Search
CPC ............ A61N 1/36139; A61N 1/36067; A61N 1/3613; A61N 1/3615; A61N 1/36171;
(Continued)

(56) References Cited

U.S. PATENT DOCUMENTS 8,929,991 B2   1/2015  Fowler et al.
9,974,959 B2   5/2018  Moffitt et al.
(Continued)

FOREIGN PATENT DOCUMENTS

WO   WO-2016144940 A1 *  9/2016  ........... A61N 1/0534
WO      2017158067 A1     9/2017

OTHER PUBLICATIONS

Hooper et al., "Dyskinetic Storm Induced by Intra-Operative Deep Brain Stimulator Placement," The Open Neurosurgery Journal, vol. 2, No. 1, Feb. 2009, 3 pp.
(Continued)

*Primary Examiner* — Mallika D Fairchild
(74) *Attorney, Agent, or Firm* — Shumaker & Sieffert, P.A.

(57) ABSTRACT

Devices, systems, and techniques are described for identifying stimulation parameter values based on electrical stimulation that induces dyskinesia for the patient. For example, a method may include controlling, by processing circuitry, a medical device to deliver electrical stimulation to a portion of a brain of a patient, receiving, by the processing circuitry, information representative of an electrical signal sensed from the brain after delivery of the electrical stimulation, determining, by the processing circuitry and from the information representative of the electrical signal, a peak in a spectral power of the electrical signal at a second frequency lower than a first frequency of the electrical stimulation, and responsive to determining the peak in the spectral power of the electrical signal at the second frequency, performing, by the processing circuitry, an action.

27 Claims, 11 Drawing Sheets

(52) U.S. Cl.
CPC ..... *A61N 1/36067* (2013.01); *A61N 1/36135* (2013.01); *A61N 1/36171* (2013.01)

(58) Field of Classification Search
CPC .............. A61N 1/0534; A61N 1/36135; A61N 1/36185; A61B 5/337
See application file for complete search history.

(56) References Cited

U.S. PATENT DOCUMENTS

| | | | |
|---|---|---|---|
| 2012/0191157 | A1 | 7/2012 | Stypulkowski et al. |
| 2012/0226330 | A1* | 9/2012 | Kolen ................ A61N 1/36003 607/48 |
| 2015/0202447 | A1* | 7/2015 | Afshar ............... A61N 1/36171 600/378 |
| 2016/0319355 | A1 | 11/2016 | Charles et al. |
| 2018/0085572 | A1 | 3/2018 | Stanslaski et al. |
| 2018/0110991 | A1 | 4/2018 | Molnar et al. |
| 2018/0272142 | A1 | 9/2018 | Zhang et al. |
| 2018/0353759 | A1 | 12/2018 | Starr et al. |
| 2019/0110754 | A1 | 4/2019 | Rao et al. |
| 2019/0388679 | A1 | 12/2019 | Geva et al. |

OTHER PUBLICATIONS

Moyer et al., "Stimulation-Induced Dyskinesias Inform Basal Ganglia Models and the Mechanisms of Deep Brain Stimulation," The Journal of Neuroscience, vol. 27, No. 8, Feb. 21, 2007, pp. 1799-1800.
Zheng et al., "Stimulation-Induced Dyskinesia in the Early Stage after Subthalamic Deep Brain Stimulation," Stereotactic and Functional Neurosurgery, vol. 88, Nov. 20, 2009, pp. 29-34.
Swann et al., "Gamma Oscillations in the Hyperkinetic State Detected with Chronic Human Brain Recordings in Parkinson's Disease," The Journal of Neuroscience, vol. 36, No. 24, Jun. 15, 2016, pp. 6445-6458.
Bouthour et al., "Dyskinesia-Inducing Lead Contacts Optimize Outcome of Subthalamic Stimulation in Parkinson's Disease," Movement Disorders, vol. 34, No. 11, Sep. 30, 2019, pp. 1728-1734.
U.S. Appl. No. 16/945,639, filed Jul. 31, 2020, by Molina et al.
International Search Report and Written Opinion of International Application No. PCT/US2021/043360, dated Oct. 27, 2021, 10 pp.
Office Action from U.S. Appl. No. 16/945,639, dated Nov. 2, 2021, 12 pp.
Response to Office Action dated Nov. 2, 2021, from U.S. Appl. No. 16/945,639, filed Feb. 2, 2022, 12 pp.
Supplemental Amendment and Examiner Interview Summary, from U.S. Appl. No. 16/945,639, dated Feb. 8, 2022, 4 pp.
Notice of Allowance from U.S. Appl. No. 16/945,639, dated Mar. 7, 2022, 7 pp.
International Preliminary Report on Patentability from International Application No. PCT/US2021/043360 dated Feb. 9, 2023, 7 pp.

* cited by examiner

STIMULATION INDUCED NEURAL RESPONSE FOR PARAMETER SELECTION

TECHNICAL FIELD

The disclosure relates to medical devices, and more particularly, electrical stimulation and sensing.

BACKGROUND

Nervous system disorders affect millions of people, causing a degradation of life, and in some cases, death. Nervous system disorders may include disorders of the central nervous system and peripheral nervous system. Some nervous system disorders may be considered "neurological movement disorders," and may include, for example without limitation, epilepsy, Parkinson's disease (PD), essential tremor, dystonia, and multiple sclerosis (MS). Periods of involuntary movements and/or loss of muscle control may characterize neurological movement disorders.

As an example of a neurological movement disorder, PD is generally characterized by slowness of movement (akinesia and bradykinesia), muscle stiffness (rigidity), tremor at rest, and gait and balance abnormalities that may lead to an inability to perform normal daily life activities. Some patients suffering from neurological movement disorders may also develop symptoms called dyskinesias and motor fluctuations, which may be side effects of certain anti-Parkinson's medication. It is believed that PD is caused by the degeneration of dopaminergic neurons in the substantia nigra pars *compacta*, a brain structure of the basal ganglia involved in the control of movement. The loss of dopamine in the basal ganglia is believed to secondarily cause a cascade of abnormal activity in the other nuclei of the basal ganglia, thalamus and cortex. This has been detected in animals and humans as changes in neuronal firing patterns, firing frequencies, and in the tendency of these neurons to fire in an oscillatory manner. These abnormal oscillations and firing patterns are thought to underlie the classic motor symptoms of PD.

There are various approaches for treating nervous system disorders (e.g., neurological movement disorders). Therapies may include any number of possible modalities alone or in combination including, for example, electrical stimulation, magnetic stimulation, drug infusion, and/or brain temperature control.

SUMMARY

In general, the disclosure is directed to detecting a brain signal indicative of patient dyskinesia in response to deep brain stimulation (DBS) and performing an action in response to detecting the dyskinesia. In particular, a sensed electrical signal from one or more of a patient's motor cortex and subthalamic nucleus (STN) is monitored during DBS of varying amplitudes and frequencies. Based on the presence or absence of a peak in spectral power from the sensed electrical signal in response to delivering the DBS of varying parameter values, an IMD may determine one or more parameter values for electrical stimulation therapy. The IMD may then determine a therapy program that defines subsequent electrical stimulation to treat the patient's current symptoms.

Examples of the present disclosure are directed to stimulation induced neural response for stimulation parameter selection. Through stimulation, a patient's neural state may be assessed. An example IMD may deliver electrical stimulation at varying amplitudes and different electrode combinations and monitor electrical signals sensed from tissue after delivery of the stimulation. The electrical stimulation may be used to determine a patient's susceptibility to dyskinesia and various other disorders. The IMD may determine a spectral power of the sensed signals and identify any peaks in power at frequencies less than the frequency of the delivered stimulation (e.g., within a band determined to be related to a subharmonic or harmonic of the frequency of the delivered stimulation pulses or a frequency from about 45 percent to about 55 percent). A peak in the spectral power at one or more frequencies less than the frequency of stimulation may indicate that the stimulation induced dyskinesia. The same electrode combination that sensed a peak indicative of dyskinesia may be appropriate for delivering electrical stimulation because that electrode combination may target the portion of the brain responsible for patient symptoms. In this manner, a dyskinesia targeted location may be identified and addressed to provide programmed therapy to treat a disease or symptom of the disease. Further, information obtained through stimulation induced dyskinesia may be used for electrode combination and/or amplitude selection for stimulation therapy.

In one example, the disclosure is directed to a method that includes controlling, by processing circuitry, a medical device to deliver electrical stimulation at a first frequency to a portion of a brain of a patient; receiving, by the processing circuitry, information representative of an electrical signal sensed from the brain after delivery of the electrical stimulation; receiving, by the processing circuitry, information representative of an electrical signal sensed from the brain after delivery of the electrical stimulation; determining, by the processing circuitry and from the information representative of the electrical signal, a peak in a spectral power of the electrical signal at a second frequency lower than the first frequency of the electrical stimulation; and responsive to determining the peak in the spectral power of the electrical signal at the second frequency, performing, by the processing circuitry, an action.

In another example, the disclosure is directed to a system that includes processing circuitry configured to control a medical device to deliver electrical stimulation at a first frequency to a portion of a brain of a patient; receive information representative of an electrical signal sensed from the brain after delivery of the electrical stimulation; determine, from the information representative of the electrical signal, a peak in a spectral power of the electrical signal at a second frequency lower than the first frequency of the electrical stimulation; and responsive to determining the peak in the spectral power of the electrical signal at the second frequency, perform an action.

In another example, the disclosure is directed to a computer readable medium that includes instructions that, when executed, cause processing circuitry to control a medical device to deliver electrical stimulation at a first frequency to a portion of a brain of a patient. receive information representative of an electrical signal sensed from the brain after delivery of the electrical stimulation; determine from the information representative of the electrical signal, a peak in a spectral power of the electrical signal at a second frequency lower than the first frequency of the electrical stimulation; determine based on the peak in spectral power, that the electrical simulation induced dyskinesia in the patient; determine from the information representative of the electrical signal, an electrode combination that sensed the peak in the spectral power, and wherein the peak in the spectral power sensed by the electrode combination is greater in magnitude than any other peak in spectral power sensed by other electrode combinations of a plurality of electrode combinations; and adjust based on determination of the peak in spectral power, at least one therapy parameter that at least partially defines subsequent electrical stimulation deliverable to the patient.

In one example, the disclosure is directed to a method that includes controlling, by processing circuitry, a medical device to deliver a first electrical stimulation at a first frequency to a brain of a patient via a first electrode combination; receiving, by the processing circuitry, information representative of a first electrical signal sensed by a second electrode combination of a medical lead from the brain after delivery of the first electrical stimulation; determining, by the processing circuitry and from the information representative of the first electrical signal, a peak in a spectral power of the first electrical signal at a second frequency lower than the first frequency of the first electrical stimulation; controlling, by the processing circuitry, the medical device to deliver a second electrical stimulation at the first frequency to the brain of the patient via the first electrode combination; receiving, by the processing circuitry, information representative of a second electrical signal sensed by the second electrode combination from the brain after delivery of the second electrical stimulation; determining, by the processing circuitry and from the information representative of the second electrical signal, a change in a magnitude of the peak in a spectral power of the second electrical signal at the second frequency; and responsive to determining the change in the magnitude of the peak in the spectral power of the second electrical signal at the second frequency, determining, by the processing circuitry and based on the change, that the medical lead has moved with respect to the brain of the patient.

In one example, the disclosure is directed to system the includes processing circuitry configured to: control a medical device to deliver a first electrical stimulation at a first frequency to a brain of a patient via a first electrode combination; receive information representative of a first electrical signal sensed by a second electrode combination of a medical lead from the brain after delivery of the first electrical stimulation; determine, from the information representative of the first electrical signal, a peak in a spectral power of the first electrical signal at a second frequency lower than the first frequency of the first electrical stimulation; control the medical device to deliver a second electrical stimulation at the first frequency to the brain of the patient via the first electrode combination; receive information representative of a second electrical signal sensed by the second electrode combination from the brain after delivery of the second electrical stimulation; determine, from the information representative of the second electrical signal, a change in a magnitude of the peak in a spectral power of the second electrical signal at the second frequency; and responsive to determining the change in the magnitude of the peak in the spectral power of the second electrical signal at the second frequency, determine, based on the change, that the medical lead has moved with respect to the brain of the patient.

In one example, the disclosure is directed to computer-readable medium that includes instructions that, when executed, cause processing circuitry to: control a medical device to deliver a first electrical stimulation at a first frequency to a brain of a patient via a first electrode combination; receive information representative of a first electrical signal sensed by a second electrode combination of a medical lead from the brain after delivery of the first electrical stimulation; determine, from the information representative of the first electrical signal, a peak in a spectral power of the first electrical signal at a second frequency lower than the first frequency of the first electrical stimulation; control the medical device to deliver a second electrical stimulation at the first frequency to the brain of the patient via the first electrode combination; receive information representative of a second electrical signal sensed by the second electrode combination from the brain after delivery of the second electrical stimulation; determine, from the information representative of the second electrical signal, a change in a magnitude of the peak in a spectral power of the second electrical signal at the second frequency; and responsive to determining the change in the magnitude of the peak in the spectral power of the second electrical signal at the second frequency, determine, based on the change, that the medical lead has moved with respect to the brain of the patient.

The details of one or more examples of the present disclosure are set forth in the accompanying drawings and the description below. Other features, objects, and advantages of the techniques discussed in this disclosure will be apparent from the description and drawings, and from the claims.

DETAILED DESCRIPTION

Figure 1:
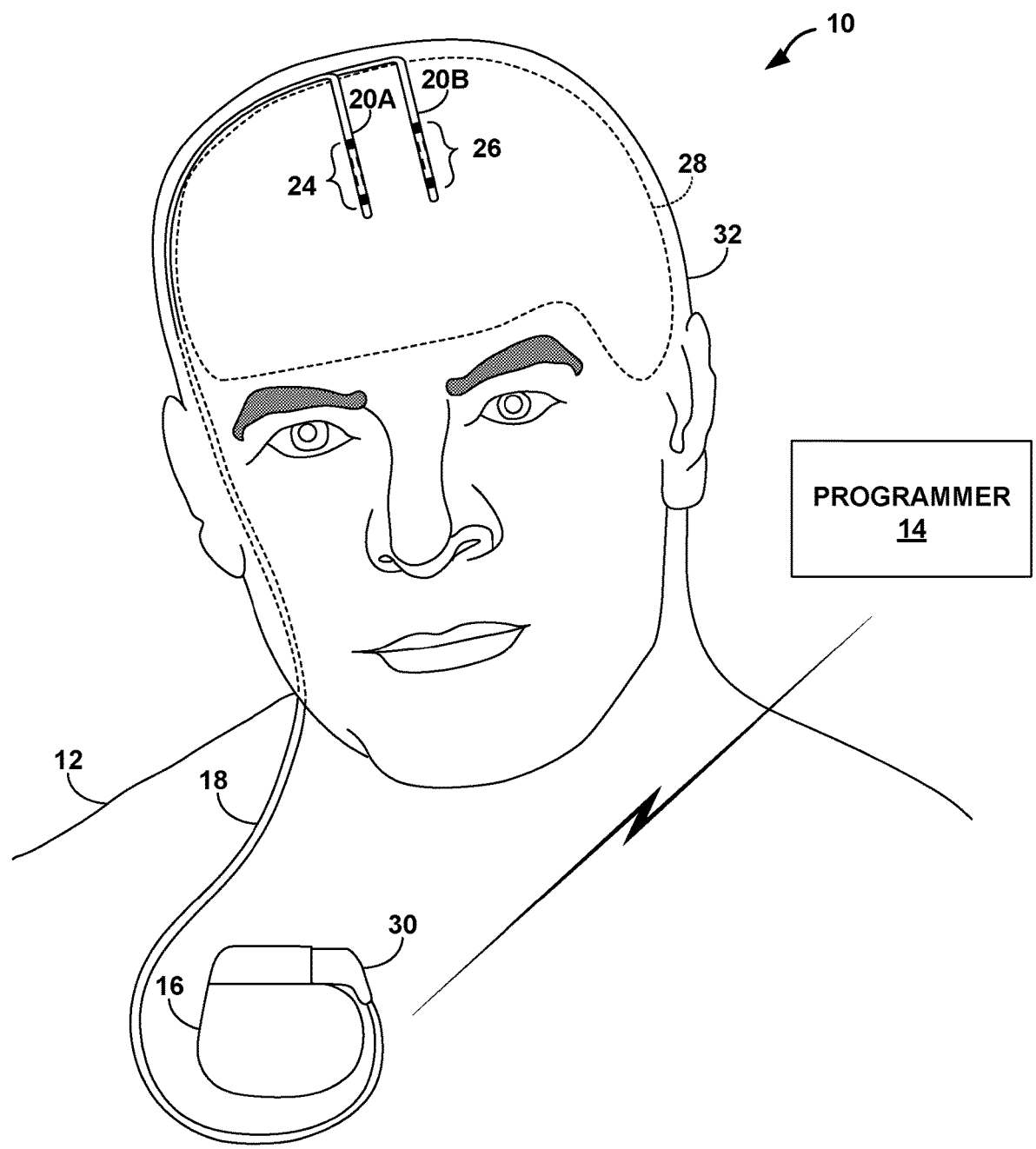
FIG. 1 is a conceptual diagram illustrating an example deep brain stimulation (DBS) system that may implement various techniques of this disclosure.

This disclosure describes to devices, systems, and techniques related to identifying signals indicative of stimulation induced dyskinesia and performing a responsive action such as selecting a parameter value for stimulation therapy or detecting movement of electrodes with respect to patient anatomy. Typical brain function generates brain signals having different frequencies, which may sometimes manifest as oscillations at a particular frequency or within a particular frequency band. Gamma frequency band oscillations, e.g., ordinarily between about 30 Hertz (Hz) and about 100 Hz or more, in the central nervous system (CNS), recorded using local field potentials (LFP), for example, may be associated with normal information processing in movement and sensory structures. Beta frequency band oscillations between about 12 Hz and about 30 Hz, have been associated with dysfunctions of CNS circuits that control behavioral movements and cognitive states. Electrical stimulation, e.g., about 130 Hz, delivered to subcortical brain areas associated with movement, e.g., STN, globus pallidus internus, and ventralis intermedius nucleus of the thalamus, may reduce symptoms associated with essential tremor and Parkinson's disease (PD) such as rigidity, bradykinesia and tremor. However, delivering electrical stimulation to the desired anatomical region that reduces symptoms while limiting undesirable side effects can be difficult and time intensive. For example, a clinician may use trial and error to identify appropriate electrode combinations, stimulation amplitude, or other stimulation parameters that efficacious therapy.

Techniques of the present disclosure are directed to identifying characteristics of sensed brain signals representative of a stimulation induced neural response indicative of dyskinesia. A system may select one or more stimulation parameter values, determine lead movement, or otherwise monitor therapy efficacy based on the induced neural response indicative of dyskinesia. Brain signals sensed from PD patients may include one or more biomarkers that may be used to indicate when adjustments to patient treatment may be beneficial. Brain signals may be collected from, for example, the patient's motor cortex, zona incerta (Zi), STN, basal ganglia, cerebellum, pedunculopontine nucleus, red nucleus, or lateral globus pallidus. The signals from the motor cortex may be collected from the primary motor cortex (M1), the premotor cortex, the supplementary motor area (SMA), the posterior parietal cortex, or the primary somatosensory cortex. One or more biomarkers may be identified in the signals collected from each region of the brain. A PD patient's motor cortex and STN may generate signals that may include several biomarkers. For example, an LFP signal sensed from a PD patient's motor cortex may include a peak in the gamma band when delivered electrical stimulation has been provided with an intensity causing dyskinesia. This peak may be at a frequency approximately half the frequency at which stimulation pulses were delivered. A peak may also appear in the lower end of the beta range with a high amplitude, when a patient is experiencing dyskinesia. As the dyskinesia subsides, the frequency of the peak in the beta band can increase while the amplitude decreases.

In this manner, a system can monitor brain activity after stimulation for biomarkers (e.g., peaks at certain frequencies and/or amplitudes) identified from measured LFP signals from the patient's brain (e.g., the motor cortex and/or STN). A system may include one or more of an implantable medical device (IMD), external programmer, or other controller that may receive LFP signals and monitor the LFP signals over time. The system may identify characteristics (e.g., one or more peaks or the absence of one or more peaks at certain frequencies or frequency bands) of the LFPs to assess whether delivered stimulation has induced dyskinesia in the patient, at what amplitude of stimulation the dyskinesia occurs, and the patient's current disease state, for example. In some examples, the system may select an electrode combination for stimulation based on which electrode combination detected a peak at a certain frequency in the LFPs. In some examples, the system may generate a dyskinesia tuning curve based on the characteristics of the LFPs that identifies a range of amplitudes of stimulation associated with dyskinesia and/or associated with acceptable stimulation in which dyskinesia is not induced. Generally, stimulation parameter values may be selected in order to avoid inducing dyskinesia while treating neurological conditions. Further, the system may monitor one or more characteristics of LFPs periodically or in response to a trigger event to control the IMD to deliver therapy such as modifying acceptable parameter values ranges (e.g., amplitude ranges) or otherwise customizing therapy for the patient. In other examples, the system may identify when a lead has moved (e.g., rotated or shifted longitudinally) in the patient's brain which may require selection of a different electrode combination for subsequent stimulation. The system may identify this lead movement by comparing characteristics of the newly sensed LFP signals by one or more electrode combinations to characteristics of past recorded LFP signals by the one or more electrode combinations, where the characteristics may be indicative of stimulation induced dyskinesia.

Certain examples consistent with the present disclosure include an implantable medical device and/or lead system adapted to electrically stimulate targets in the brain to induce dyskinesia. The IMD may automatically deliver a sweep of stimulation pulses having an increasing and/or decreasing stimulation amplitude value or provide for manual adjustment of stimulation amplitude to induce dyskinesia. The IMD may deliver the sweep of amplitudes for one electrode combination or for two or more electrode combinations in order to identify which electrode combination induces dyskinesia. The system may detect dyskinesia by identifying a peak within a power spectrum of received LFPs after stimulation recorded by one or more electrode combinations. In some examples, the peak may occur at a frequency approximately 50% of the frequency (e.g., between 45-55% of the delivered stimulation pulse frequency). The peak may occur in the gamma frequency band between 30 and 100 Hz. For example, a peak marker may be found at half the stimulation frequency (e.g., 160 Hz stimulation frequency may elicit a peak at approximately 80 Hz when dyskinesia was induced) and may have a distinct "thin" width to the peak in this frequency range. In contrast, intrinsic physiological signals may have a broader peak encompassing a larger range of frequencies at that elevated amplitude of the peak.

Dyskinesia resulting from stimulation above a certain threshold intensity is a normal response, and such dyskinesia may indicate that the stimulation was delivered to a region of the brain associated with movement disorders. Stimulation induced dyskinesia may be observed in sensed electrical signals from the brain, such as LFPs. Examples of the present disclosure relate to using non-therapeutic stimulation to induce dyskinesia, but the stimulation may, in some examples, result in therapeutic effects for some patients. Through the delivered stimulation configured to induce dyskinesia, the system may identify one or more stimulation parameter values that at least partially define stimulation that may provide therapy to the patient, such as a reduction or elimination of tremor, dyskinesia, or bradykinesia. Through stimulation induced dyskinesia, a patient's neural state may be assessed, a susceptibility to dyskinesia may be assessed, and/or a dyskinesia targeted location may be discovered and addressed to provide therapy for the disease.

In some examples, the system may use characteristics associated with detected stimulation induced dyskinesia to select one or more electrode combinations, amplitude values (e.g., maximum values, minimum values, or associated ranges), pulse widths, or any other parameter values that may at least partially define therapeutic electrical stimulation. Additionally, or alternatively, the system may detect lead movement, such as lead rotation, by comparing changes to sensed peaks associated with stimulation induced dyskinesia. For example, the system may determine that the lead has moved (e.g., longitudinally or rotationally) if the system identifies a change to the magnitude of a peak (e.g., a smaller or absent peak) in the spectral power of an electrical signal sensed by an electrode combination from the peak indicative of stimulation induced dyskinesia previously detected from that electrode combination. As another example, the system may determine that the lead has moved if the system identifies a different electrode combination that is now associated with the largest magnitude of a peak in the spectral power of the electrical signal sensed by different electrode combinations of a lead. In response to detecting that the lead has moved or otherwise shifted such that the electrodes have moved relative to surrounding anatomy, the system may select new stimulation parameter values (e.g., electrode combinations and/or amplitudes) or recommend selection of new stimulation parameter values to maintain efficacious therapy using the new lead position.

The stimulation configured to induce a neural response indicative of dyskinesia may be identified using an automatic or manual sweep of amplitudes for one or more electrode combinations of one or more leads. For each electrode combination that delivers stimulation, the system may sense electrical signals from one sensing electrode combination or many electrode combinations. In this manner, the system may identify the electrode combination and amplitude values that induce dyskinesia. Once a peak indicative of dyskinesia peak is identified, then the system can determine stimulation parameter values (e.g., one or more therapy programs) that may define electrical stimulation that provides efficacious therapy without the dyskinesia used as a marker to identify such parameter values.

FIG. 1 is a conceptual diagram illustrating an example deep brain stimulation (DBS) system that may be used to implement the techniques of this disclosure. In FIG. 1, example therapy system 10 may deliver electrical stimulation therapy to control a patient condition, such as a movement disorder or other neurodegenerative impairment of patient 12. Patient 12 ordinarily will be a human patient. In some cases, however, therapy system 10 may be applied to other mammalian or non-mammalian non-human patients. While movement disorders and neurodegenerative impairment are primarily referred to in this disclosure, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as tremor, rigidity, bradykinesia, rhythmic hyperkinesia, non-rhythmic hyperkinesia, and akinesia. In some cases, the movement disorder may be a symptom of PD. However, the movement disorder may be attributable to other patient conditions. Although PD is primarily referred to throughout the remainder of the disclosure, the therapy systems and methods described herein may also be useful for controlling symptoms of other conditions, such as other movement disorders or neurodegenerative impairment.

In the example of FIG. 1, therapy system 10 includes medical device programmer 14, IMD 16, lead extension 18, and leads 20A and 20B with respective sets of electrodes 24, 26. Lead extension 18 may include a proximal connector 30 that operatively connects to the header of IMD 16. In some examples (not shown), therapy system 10 may include one or more additional medical devices, which may also be in communication with medical device programmer 14. In the example shown in FIG. 1, electrodes 24, 26 of leads 20A, 20B are positioned to sense LFPs and/or deliver electrical stimulation to a tissue site within brain 28, such as target tissue in a deep brain site under the dura mater of brain 28 of patient 12. In some examples, delivery of stimulation to one or more regions of brain 28 inside cranium 32, such as the STN, globus pallidus internus (GPi), motor cortex such as M1, or thalamus, may be an effective treatment to manage movement disorders, such as Parkinson's Disease or essential tremor.

IMD 16 includes a therapy module that includes a stimulation generator configured to generate and deliver electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination.

It should be noted that leads 20A, 20B may be separate leads, or bifurcated segments on a single lead. Some example configurations may comprise only a single lead. Two leads support bilateral stimulation in both brain hemispheres while one lead supports unilateral stimulation in one hemisphere. In some examples, one lead is positioned in or near M1 and the other lead is positioned in or near STN. In an amplitude sweep, stimulation may be applied at different amplitudes in a range of voltages in a sequence, e.g., by increasing or decreasing by N V, where N is any number, in a linear or non-linear manner.

In examples of the present disclosure, IMD 16 may search for, and detect, a brain signal indicative of patient dyskinesia induced by delivered electrical stimulation. In one example, the amplitude of successive pulses of the electrical stimulation delivered to the portion of the brain may be iteratively increased in what may be referred to as an amplitude sweep. For example, the amplitude of the electrical stimulation may be iteratively increased through a range of amplitude values that includes, or stops at, an amplitude value at which dyskinesia is induced. In an amplitude sweep, the voltage or amplitude value of pulses of the electrical stimulation may begin at one value and then may be varied, e.g., increased or decreased, from a first voltage to a second voltage. For example, two electrodes of one of leads 20A or 20B, may be used to deliver electrical stimulation to patient 12 in an amplitude sweep and IMD 16 may sense electrical signals between one or more electrode combinations to potentially detect characteristics of the sensed electrical signals indicative of the induced dyskinesia when it occurs. In some examples, IMD 16 may perform the amplitude sweep multiple times, where the patient is in a different state during each sweep. For example, a sweep may be performed while the patient is showing signs of dystonia, another sweep may be performed while the patient is within the therapeutic window, and a third sweep may be performed while the patient is sleeping. In some examples, other electrical stimulation parameters may be adjusted in a sweeping manner. For example, pulse width, stimulation frequency, and/or burst frequency may also be varied and monitored for induced dyskinesia. As one example, two electrodes of lead 20A may begin delivering electrical stimulation to patient 12 at a low frequency, which is iteratively increased to higher frequencies. For example, electrical stimulation may be delivered starting at a first frequency in the beta band to a frequency in a gamma band (e.g., from about 30 Hz to about 100 Hz) while simultaneously monitoring LFP or EEG activity. IMD 16 may complete any sweep between predetermined values or, in other examples, terminate the sweep in response to detecting that dyskinesia has been induced. IMD 16 may store the parameter values at which the dyskinesia was induced as a dyskinesia threshold value and select a parameter value below that dyskinesia threshold value for subsequent stimulation therapy.

IMD 16 may perform an action or actions in response to detecting the induced dyskinesia. In particular, a sensed electrical signal from one or more of a patient's motor cortex and subthalamic nucleus (STN) may be monitored during DBS of varying amplitudes and/or frequencies. Based on the presence or absence of a peak in spectral power from the sensed electrical signal in response to delivering the DBS of varying parameter values, IMD 16 may determine one or more parameter values for electrical stimulation therapy. For example, IMD 16 may select the electrode combination at which the highest magnitude peak indicative of induced dyskinesia was identified for subsequent stimulation therapy. As another example, IMD 16 may identify a range of amplitude values for stimulation therapy that is limited by the lowest amplitude value at which dyskinesia was induced. IMD 16 may then determine a therapy program that defines subsequent electrical stimulation to treat the patient's current symptoms. In other examples, IMD 16 may perform the action of determining lead movement (e.g., longitudinal movement or rotation) in response to determining that a peak in the spectral power of a sensed electrical signal has changed for one or more electrode combinations. This change in the peak, such as a change in the magnitude of the peak from previous sensed signals, may indicate that different electrodes are now closest to the origin of the dyskinesia signal which indicates the lead movement. In some examples, IMD 16 may perform an action such as output information representative of the sensed peak in spectral power for display by another device, such as programmer 14 or another external device.

Figure 2:
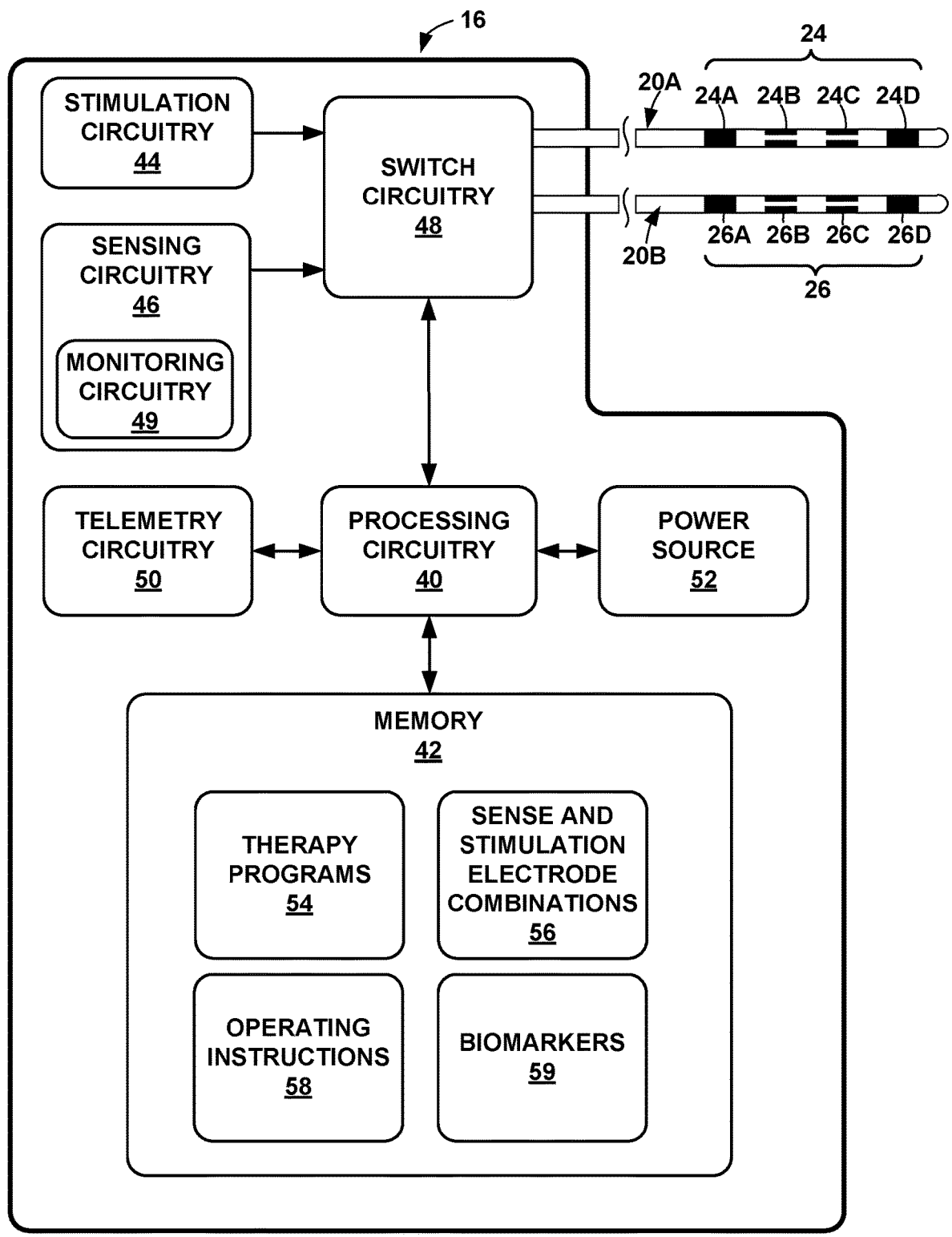
FIG. 2 is functional block diagram illustrating components of an example medical device that may implement various techniques of this disclosure.

FIG. 2 is functional block diagram illustrating components of an example medical device, such as IMD 16, that may be used to implement the techniques of this disclosure. In the example shown in FIG. 2, IMD 16 includes processing circuitry 40, memory 42, stimulation circuitry 44, sensing circuitry 46, switch circuitry 48, telemetry circuitry 50, and power source 52. Memory 42 may include any volatile or non-volatile media, such as a random-access memory (RAM), read only memory (ROM), non-volatile RAM (NVRAM), electrically erasable programmable ROM (EEPROM), flash memory, and the like. Memory 42 may store computer-readable instructions that, when executed by processing circuitry 40, cause IMD 16 to perform various functions.

In the example shown in FIG. 2, memory 42 stores therapy programs 54, sense and stimulation electrode combinations 56, and operating instructions 58 in separate memories within memory 42. Each stored therapy program 54 defines a particular program of therapy in terms of respective values for electrical stimulation parameters, such as a stimulation electrode combination, electrode polarity, current or voltage amplitude, pulse width, and pulse rate. In some examples, the therapy programs 54 may be stored as a therapy group, which defines a set of therapy programs with which stimulation may be generated. The stimulation signals defined by the therapy programs of the therapy group may be delivered together on an overlapping or non-overlapping (e.g., time-interleaved) basis. In some examples, a therapy group may include a set of therapy programs wherein each of the therapy programs is associated with dyskinesia being present in a physiological signal received from the patient's brain. In some examples, a therapy group may include a combination of stimulation parameters. In other examples, a therapy group may include a dyskinesia tuning curve that may be selected for electrode combination and/or amplitude selection. The therapy groups may be stored in memory 42, or another memory within IMD 16 or programmer 14. Memory 42 may also temporarily store the most recently determined dyskinesia (e.g., the frequency and amplitude of the last stimulation signal that induced dyskinesia, the electrode combination used to induce and/or sense the dyskinesia, and the power spectrum of the sensed dyskinesia), and the therapy program currently being applied to the patient.

Sense and stimulation electrode combinations 56 include sense electrode combinations and associated stimulation electrode combinations. As described above, in some examples, the sense and stimulation electrode combinations may include the same subset of electrodes 24, 26, or may include different subsets of electrodes. Operating instructions 58 guide general operation of IMD 16 under control of processing circuitry 40 and may include instructions for measuring the impedance of electrodes 24, 26 or possibly performing a lead integrity test. IMD 16 may perform lead integrity testing in response to certain events, such as a determination that a previously identified peak indicative of induced dyskinesia is no longer present for a particular electrode combination. Lead functionality closed-looping, e.g., lead impedance or current closed-looping, may be performed using any known techniques. For example, to perform lead integrity testing, IMD 16 may deliver a non-therapeutic pulse via a combination of two electrodes, measure final voltage or current amplitude for the pulse, and determine an impedance for the combination based on the measured final amplitude. Testing may be repeated for a plurality of electrode combinations and/or for the same combinations of electrodes on multiple occasions according to the instructions stored by IMD 16. A lead, or circuit of a lead, may fail the lead integrity test when the measured impedance within a circuit exceeds a predetermined threshold that may be indicative of a conductor fracture.

Processing circuitry 40 may compare characteristics of received bioelectrical brain signals, such as one or more features within power spectrums of LFPs, to bioelectrical brain signal values stored as biomarkers 59, as will be discussed in more detail below.

Stimulation circuitry 44, under the control of processing circuitry 40, generates stimulation signals for delivery to patient 12 via selected combinations of electrodes 24, 26. An example range of electrical stimulation parameters believed to be effective in DBS to manage a movement disorder of patient include the following:

1. Frequency: between approximately 20 Hz and approximately 500 Hz, such as between approximately 50 Hz and approximately 150 Hz, or approximately 130 Hz.

2. Voltage Amplitude: between approximately 0.1 volts and approximately 20 volts, such as between approximately 0.5 volts and approximately 10 volts, or approximately 5 volts.

3. Current Amplitude: a current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamp and approximately 40 milliamps, or approximately 10 milliamps. However, in some examples, the impedance may range between about 200 ohms and about 2 kilohms.

4. Pulse Width: between approximately 10 microseconds and approximately 5000 microseconds, such as between approximately 100 microseconds and approximately 1000 microseconds, or between approximately 180 microseconds and approximately 450 microseconds.

Stimulation circuitry 44 may, for example, generate either constant current-based or constant voltage-based stimulation in the form of pulses or continuous waveforms. In delivering constant current-based stimulation, stimulation circuitry 44 maintains the amplitude of the current at a constant level. In delivering constant voltage-based stimulation, stimulation circuitry 44 maintains the amplitude of the voltage at a constant level. In other examples, stimulation circuitry 44 may generate bipolar stimulation.

Accordingly, in some examples, stimulation circuitry 44 generates electrical stimulation signals in accordance with the electrical stimulation parameters noted above. Other ranges of therapy parameter values may also be useful and may depend on the target stimulation site within patient 12, which may be within brain 28 or other portions of the nervous system. While stimulation pulses are described, stimulation signals may be of any form, such as continuous-time signals (e.g., sine waves) or the like.

Processing circuitry 40 may include any one or more of a microprocessor, a controller, a digital signal processor (DSP), an application specific integrated circuit (ASIC), a field-programmable gate array (FPGA), discrete logic circuitry, and the functions attributed to processing circuitry 40 in this disclosure may be embodied as firmware, hardware, software or any combination thereof. In some examples, the DSP may use a fast Fourier transform (FFT) algorithm. Processing circuitry 40 controls stimulation circuitry 44 according to therapy programs 54 stored in memory 42 to deliver, or apply, particular stimulation parameter values specified by one or more of programs, such as amplitude, pulse width, and pulse rate.

In one example, the set of electrodes 24 includes electrodes 24A, 24B, 24C, and 24D, and the set of electrodes 26 includes electrodes 26A, 26B, 26C, and 26D. In the example shown in FIG. 2, electrodes 24B, 24, 26B, and 26C are each multiple independently configurable electrodes (e.g., three electrodes) disposed at different circumferential positions around the perimeter of the respective lead 20A and 20B. Although electrodes 24A, 24D, 26A, and 26D are shown as ring electrodes, any of these ring electrodes may alternatively be replaced by two or more electrodes disposed around the perimeter of the lead at the same axial position. Processing circuitry 40 also controls switch circuitry 48 to apply the stimulation signals generated by stimulation circuitry 44 to selected combinations of electrodes 24, 26. In particular, switch circuitry 48 may couple stimulation signals to selected conductors within leads 20, which, in turn, deliver the stimulation signals across selected electrodes 24, 26. Switch circuitry 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation circuitry 44 is coupled to electrodes 24, 26 via switch circuitry 48 and conductors within leads 20. In some examples, however, IMD 16 does not include switch circuitry 48.

Stimulation circuitry 44 may be a single channel or multi-channel stimulation generator. In particular, stimulation circuitry 44 may be capable of delivering a single stimulation pulse, multiple stimulation pulses or continuous signal at a given time via a single electrode combination, or multiple stimulation pulses or continuous signals at a given time via multiple electrode combinations. In some examples, however, stimulation circuitry 44 and switch circuitry 48 may be configured to deliver multiple channels on a time-interleaved basis. For example, switch circuitry 48 may serve to time divide the output of stimulation circuitry 44 across different electrode combinations at different times to deliver multiple programs or channels of stimulation energy to patient 12.

Sensing circuitry 46, under the control of processing circuitry 40, may sense bioelectrical brain signals and provide the sensed bioelectrical brain signals to processing circuitry 40. Processing circuitry 40 may control switch circuitry 48 to couple sensing circuitry 46 to selected combinations of electrodes 24, 26, i.e., a sense electrode combination. In this way, IMD 16 is configured such that sensing circuitry 46 may sense bioelectrical brain signals, such as LFPs, with a plurality of different sense electrode combinations. Switch circuitry 48 may be electrically coupled to the selected electrodes 24, 26 via the conductors within the respective leads 20, which, in turn, deliver the bioelectrical brain signals sensed across the selected electrodes 24, 26 to sensing circuitry 46. The bioelectrical brain signals may include biomarkers, e.g., amplitudes, phase relationships, or other characteristics, which are indicative of electrical activity within brain 28 of patient 12 and, in particular, electrical activity within one or more frequency bands, e.g., gamma frequency band, beta frequency band, and other frequency bands, of brain 28.

Although sensing circuitry 46 is incorporated into a common housing with stimulation circuitry 44 and processing circuitry 40 in FIG. 2, in other examples, sensing circuitry 46 may be in a separate housing from IMD 16 and may communicate with processing circuitry 40 via wired or wireless communication techniques. Example bioelectrical brain signals include, but are not limited to, a signal generated from LFPs within one or more regions of brain 28. EEG and ECoG signals are other examples of bioelectric brain signals that may be measured from brain 28.

Processing circuitry 40 may analyze bioelectrical brain signals in order to determine, for example, whether one or more biomarkers is present within one or more of the beta frequency band, and the gamma frequency band of the patient's motor cortex or STN. For example, sensing circuitry 46 may sense via a subset of electrodes 24, 26 (or a different subset of electrodes) bioelectrical brain signals of brain 28, measure an amplitude of the sensed bioelectrical brain signals, and provide the sensed bioelectrical brain signals and measured amplitude to processing circuitry 40. Typically, the subset of electrodes, or electrode combination, used to sense bioelectric brain signals are located on the same lead. However, in other examples, electrodes of an electrode combination may be located on different leads and/or on the housing of IMD 16. Upon receiving the sensed bioelectrical brain signals and measured amplitude, processing circuitry 40 may analyze the received signals to determine whether a peak is present in the power spectrum of the sensed electric signal. For example, processing circuitry 40 may analyze the power spectrum to identify a peak at approximately half (e.g., 45% to 55%) of the frequency of the pulse frequency of stimulation that induced the peak. For example, this peak may be a biomarker indicative of induced dyskinesia when the peak is present at approximately 70-80 Hz when the pulse frequency was approximately 150 Hz. Such a peak may be indicative of signals originating from either the motor cortex signal or the STN. In some examples, any detected peaks in the power spectrum may be compared to peaks or other characteristics of predetermined dyskinesia events 59. In some examples, processing circuitry 40 may also determine the amplitude of any peaks to determine if the peaks have an amplitude above a threshold amplitude. The threshold amplitude may be an absolute amplitude, an amplitude above signal magnitude of adjacent frequencies, or a percentage of the signal magnitude of adjacent frequencies. In some examples, the exact frequency at which processing circuitry 40 identifies for peaks indicative of induced dyskinesia may be determined on a patient specific basis. These exact frequencies or frequency banes may be stored in biomarkers 59.

In accordance with the techniques of this disclosure, processing circuitry 40 may select a therapy program from a plurality of therapy programs stored in memory 42. For example, processing circuitry 40 may select a first program that defines an amplitude or allows a patient to select from a range of amplitudes, of a stimulation signal at a frequency range that has induced dyskinesia at higher amplitudes. In some examples, processing circuitry 40 may select a program that titrates therapy to an amplitude appropriate for the patient that is below the amplitude at which prior stimulation induced dyskinesia. Such an amplitude below the level that induced dyskinesia may reduce other symptoms of the patient without inducing dyskinesia. A spike may refer to a peak with an amplitude above a predetermined threshold, or where the ratio of the amplitude to the base of the peak is above a predetermined ratio. In some examples, the first and second programs may be patient specific. For example, the first program may include delivery of stimulation at a particular amplitude determined during initial programming of the IMD 16. Similarly, the second program may include delivery of stimulation at a second particular amplitude determined during initial programming of the IMD 16.

Sensing circuitry 46 may include frequency monitoring circuitry 49 capable of monitoring bioelectrical brain signals associated with patient 12 in selected frequency bands. Frequency monitoring circuitry 49 may include tunable filtering and amplification capabilities that filter the bioelectrical brain signals into one or more of the beta frequency band, the gamma frequency band, and the theta frequency band (4-7 Hz), for example, and amplify the resulting filtered signal for analysis by processing circuitry 40. That is, frequency monitoring circuitry 49 may be tuned, either by a clinician, patient, or without user intervention (i.e., automatically), to detect bioelectrical brain signals in one or more frequency bands such as the beta frequency band, or the gamma frequency band. It should be noted that in some example implementations, the bioelectrical brain signals of patient 12 may be analyzed by processing circuitry 60 of programmer 14 (or by a computer) and then transmitted via telemetry circuitry 64 to telemetry circuitry 50 of IMD 16.

After stimulation circuitry 44 delivers the stimulation that induced dyskinesia and determines the amplitude that induced dyskinesia, the sensing circuitry 46 and frequency monitoring circuitry 49 may again monitor bioelectrical brain signals associated with patient 12. Then, processing circuitry 40 may analyze the sensed signals to determine whether the delivered electrical stimulation subsequently induced dyskinesia. Based on whether dyskinesia was induced, processing circuitry 40 may modify the therapy being provided to patient 12. Modification may include selecting a different therapy program from memory 42 or adjusting one or more stimulation parameters. For example, if processing circuitry 40 determines that stimulation induced dyskinesia, processing circuitry 40 may reduce the amplitude of stimulation until dyskinesia is no longer induced.

The examples described above may utilize closed-loop techniques for the delivery of electrical stimulation. That is, the examples describe sensing circuitry 46 and frequency monitoring circuitry 49 monitoring bioelectrical brain signals, processing circuitry 40 analyzing the bioelectrical brain signals and controlling delivery of electrical stimulation based on the analysis, sensing circuitry 46 and frequency monitoring circuitry 49 monitoring bioelectrical brain signals after delivery of the electrical stimulation, and processing circuitry 40 determining whether stimulation circuitry 44 should again deliver electrical stimulation.

The techniques described in this disclosure may be performed in a system that has already been implanted in a patient and programmed, or in clinical settings in which a system is being implanted in a patient and programming is being turned on for the first time. In a clinical implant setting, for example, in addition to or instead of monitoring dyskinesia inducement, a clinician may monitor the motor performance, e.g. using the clinical Unified Parkinson's Disease Rating Scale (UPDRS), or similar clinical measure, of a patient. The clinician may use the combination of observed motor performance and bioelectrical signals collected to better identify patient dyskinesia. A clinician may also use the techniques of this disclosure to deliver electrical stimulation to patient 12 and monitor the motor performance of patient 12 in response to receiving the electrical stimulation. By monitoring the motor performance of patient 12 in response to receiving the electrical stimulation, a clinician may determine efficacious electrical stimulation settings that may be programmed into memory 42. For example, a clinician may determine the patient's efficacious electrical stimulation in a variety of patient states. The patient states may include an unmedicated state where the patient is not receiving any therapy and is displaying symptoms of PD such as bradykinesia, rigidity, dystonia, or tremor; an equilibrium state where the patient's response to therapy includes PD symptoms under control, possibly with medication, without the presence of side effects; and a side effects state, where the patient is experiencing side effects from over medication or stimulation such as dyskinesia. The determined stimulation settings may be programmed into memory 42 as part of therapy programs 54 for later use.

Telemetry circuitry 50 supports wireless communication between IMD 16 and an external programmer 14 or another computing device under the control of processing circuitry 40. In some examples, telemetry circuitry 50 may support communication between IMD 16 and another medical device (not shown). Processing circuitry 40 of IMD 16 may receive, as updates to programs, values for various stimulation parameters such as amplitude and electrode combination, from programmer 14 via telemetry circuitry 50. The updates to the therapy programs may be stored within therapy programs 54 portion of memory 42. Telemetry circuitry 50 in IMD 16, as well as telemetry modules in other devices and systems described herein, such as programmer 14, may accomplish communication by radiofrequency (RF) communication techniques. In addition, telemetry circuitry 50 may communicate with external medical device programmer 14 via proximal inductive interaction of IMD 16 with programmer 14. Accordingly, telemetry circuitry 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Examples of the present disclosure are directed to selecting stimulation parameter values based on stimulation induced dyskinesia. Through stimulation, a patient's neural state may be assessed. IMD 16 may deliver electrical stimulation at varying amplitudes and different electrode combinations and monitor electrical signals sensed from tissue after delivery of the stimulation. The electrical stimulation may be used to determine a patient's susceptibility to dyskinesia and various other disorders. IMD 16 may determine a spectral power of the sensed signals and identify any peaks in the spectral power at frequencies less than the frequency of the delivered stimulation (e.g., about 45 percent to 55 percent of the frequency of delivered stimulation pulses). A peak in the spectral power at one or more frequencies less than the frequency of stimulation may indicate that the stimulation induced dyskinesia. The same electrode combination that sensed a peak indicative of dyskinesia may be appropriate for delivering electrical stimulation because that electrode combination may be closest to the portion of the brain responsible for causing dyskinesia and patient symptoms. In this manner, a dyskinesia associated targeted location may be identified and addressed to provide programmed therapy to treat a disease or symptom of the disease. Further, information obtained through stimulation induced dyskinesia may be used for electrode combination and/or amplitude selection for stimulation therapy.

Figure 3:
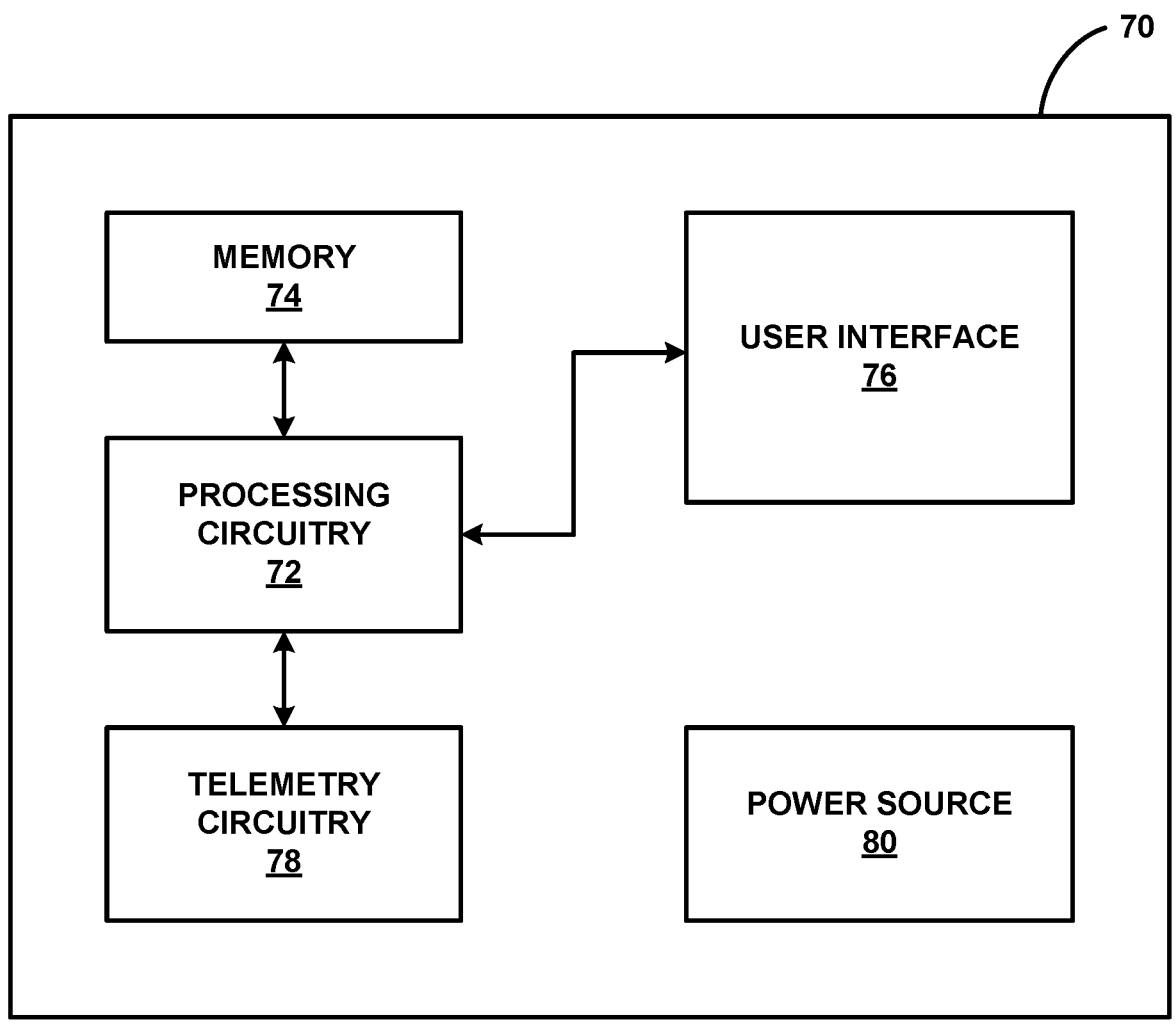
FIG. 3 is a block diagram illustrating an example configuration of an external programmer.

FIG. 3 is a block diagram illustrating an example configuration of an external programmer 70. While programmer 70 may generally be described as a hand-held computing device, the programmer may be a notebook computer, a cell phone, or a workstation, for example. In the example of FIG. 3, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 12 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 61 may include an antenna, which may take on a variety of forms, such as an internal or external antenna. In some examples, IMD 16 may transmit information representative of the determined spectral power of sensed electrical signals for one or more electrode combinations, peaks in the spectral power, other information related to induced dyskinesia, parameters associated with induced dyskinesia, or recommended parameter values for subsequent electrical stimulation. Processing circuitry 72 may control user interface 76 to present this information to the user and/or receive user input selecting parameter values and/or confirming recommended parameter values for subsequent stimulation parameters. Processing circuitry 72 may transmit these parameter values to IMD 16 to define stimulation to be delivered to the patient.

Examples of local wireless communication techniques which may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

Figure 4A:
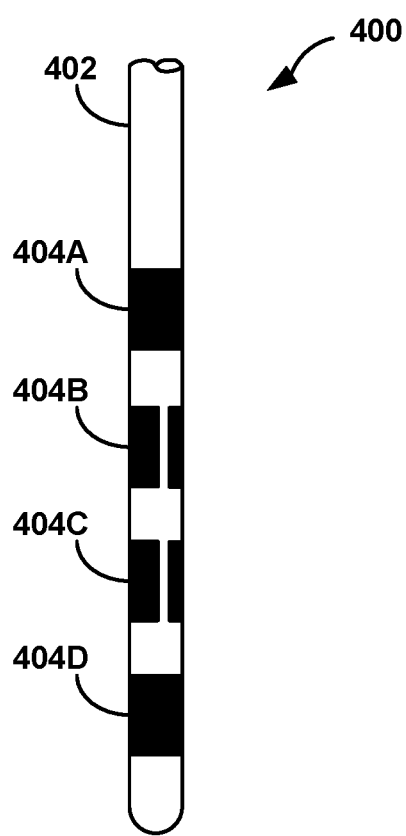
FIGS. 4A and 4B are conceptual diagrams of example leads with respective electrodes carried by the lead.
Figure 4B:
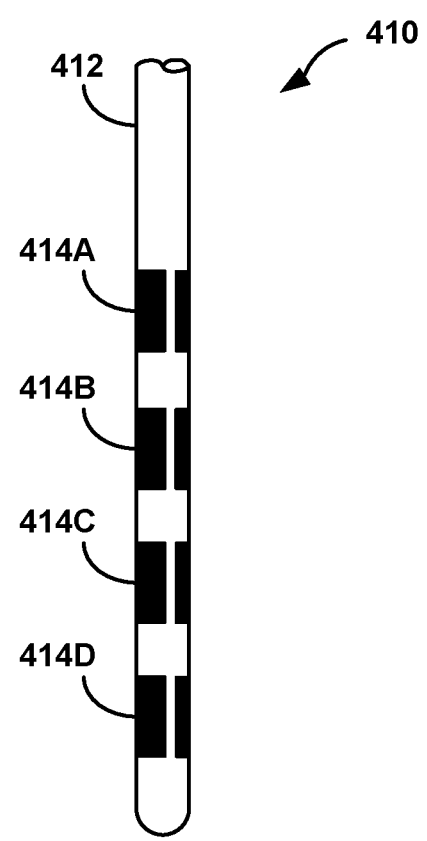

FIGS. 4A and 4B are conceptual diagrams of example leads 400 and 410, respectively, with respective electrodes carried by the lead. As shown in FIGS. 4A and 4B, leads 400 and 410 are example configurations that may be similar to leads 20A and 20B shown in FIG. 1. As shown in FIG. 4A, lead 400 includes four electrode levels 404 (includes levels 404A-404D) mounted at various lengths of lead housing 402. Lead 400 is inserted into through cranium 32 to a target position within brain 28.

Lead 400 is implanted within brain 28 at a location determined by the clinician to be near an anatomical region to be stimulated. Electrode levels 404A, 404B, 404C, and 404D may be equally spaced along the axial length of lead housing 402 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include one or more radiopaque stripes or other radiopaque orientation markers (not shown) along the outside of the lead housing. The radiopaque stripe corresponds to a certain circumferential location that allows lead 400 to be imaged when implanted in patient 12. Using the images of patient 12, the clinician can use the radiopaque stripe as a marker for the exact orientation of lead 400 within the brain of patient 12. Orientation of lead 400 may be needed to easily program the stimulation parameters by generating the correct electrode configuration to match the stimulation field defined by the clinician. In other embodiments, a marking mechanism other than a radiopaque stripe may be used to identify the orientation of lead 400. These marking mechanisms may include something similar to a tab, detent, or other structure on the outside of lead housing 402. In some embodiments, the clinician may note the position of markings along a lead wire during implantation to determine the orientation of lead 400 within patient 12.

FIG. 4B illustrates lead 410 that includes multiple electrodes at different respective circumferential positions at each of levels 414A-414D. Similar to lead 400, lead 410 is inserted through a burr hole in cranium 32 to a target location within brain 28. Lead 410 includes lead housing 412. Four electrode levels 414 (414A-414D) are located at the distal end of lead 410. Each electrode level 414 is evenly spaced from the adjacent electrode level and includes two or more electrodes. In one example, each electrode level 414 includes three, four, or more electrodes distributed around the circumference of lead housing 412. Therefore, lead 410 includes electrodes 414. Each electrode may be substantially rectangular in shape. Alternatively, the individual electrodes may have alternative shapes, e.g., circular, oval, triangular, rounded rectangles, or the like.

In alternative examples, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 28 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other embodiments, leads 400 or 410 may be shaped differently than a cylinder. For example, the leads may include one or more curves to reach target anatomical regions of brain 28. In some embodiments, leads 400 or 410 may be similar to a flat paddle lead or a conformable lead shaped for patient 12. Also, in other embodiments, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402.

Figure 5A:
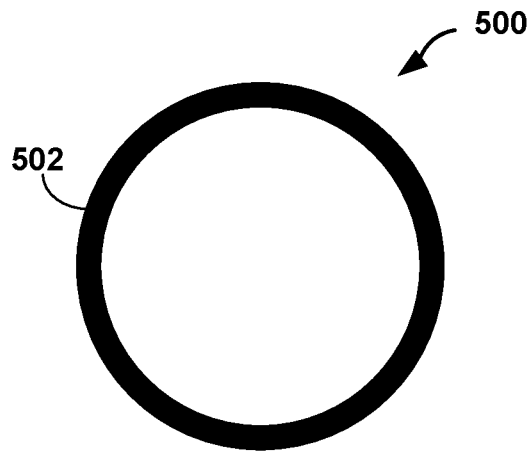
FIGS. 5A, 5B, 5C, and 5D are conceptual diagrams of example electrodes disposed around a perimeter of a lead at a particular longitudinal location.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by the user interface.

Figure 5B:
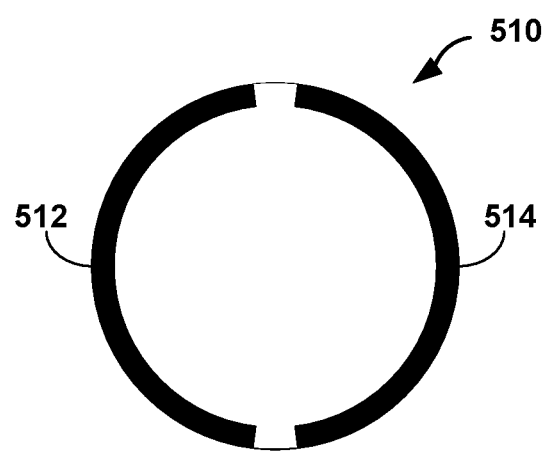

FIG. 5B shows electrode level 510 that includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

Figure 5C:
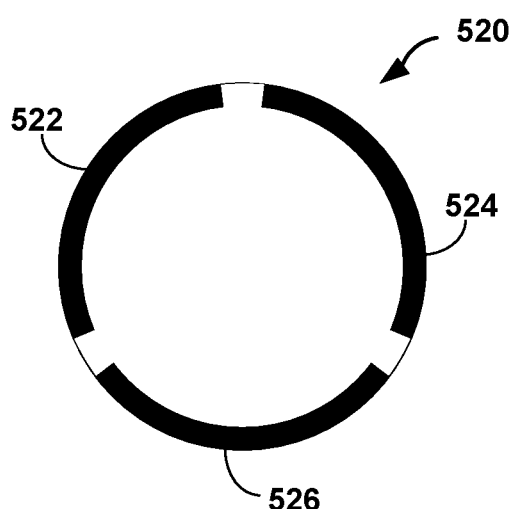

FIG. 5C shows electrode level 520 that includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

Figure 5D:
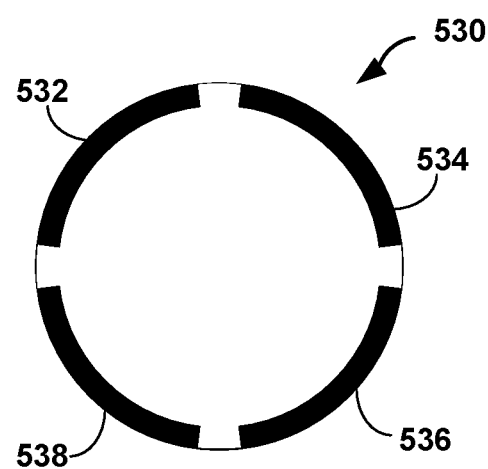

FIG. 5D shows electrode level 530 that includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other embodiments, up to ten or more electrodes may be included within an electrode level. In alternative embodiments, consecutive electrode levels of lead 20A & 20B may include a variety of electrode levels 500, 510, 520, and 530. For example, lead 20A or 20B (or any other lead described herein) may include electrode levels that alternate between electrode levels 510 and 530 depicted in FIGS. 5B and 5D. In this manner, various stimulation field shapes may be produced within brain 28 of patient 12. Further the above-described sizes of electrodes within an electrode level are merely examples, and the description is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted at tissues needing certain shaped stimulation fields.

Figure 6:
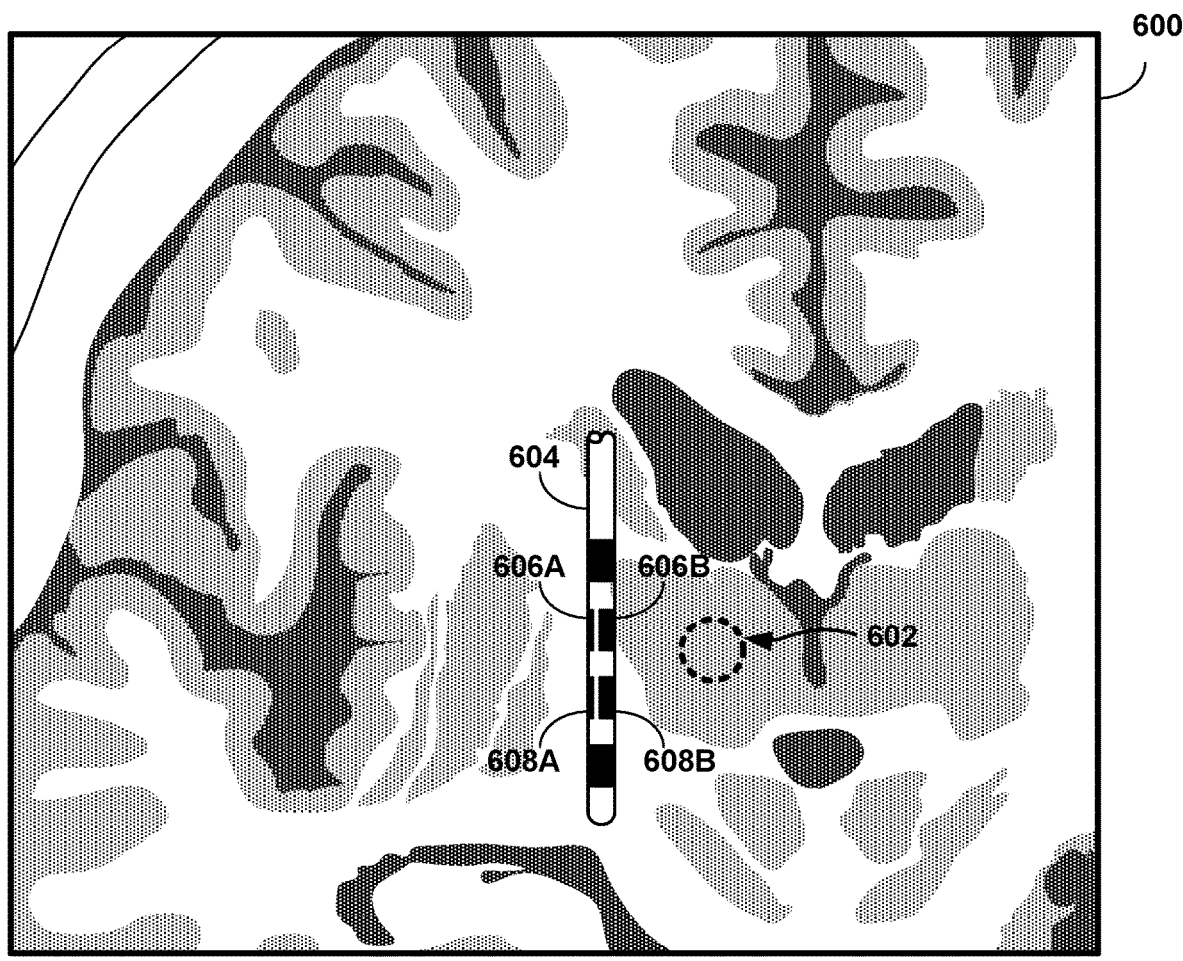
FIG. 6 is a coronal view of example tissue with a lead placed with respect to a target location within tissue.

FIG. 6 is a coronal view of example tissue with a lead 604 placed offset with respect to a target location within tissue. As shown in FIG. 6, a representation of anatomical regions of brain 28 is displayed by coronal view 600. Coronal view 600 is a front-back vertical section of brain 28. Coronal view 600 may be an actual image of brain 28 produced with magnetic resonance imaging (MM), computed tomography (CT), or another imaging modality. Coronal view 600 may be an illustration of the location of a lead with respect to a target tissue 602 from which electrical signals originate (e.g., LFP signals). In some examples, coronal view 600 may be presented by programmer 70, for example on a display of user interface 76, or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 28. Differently shaded portions of coronal view 600 indicate varying densities of tissue within brain 28. Darker portions indicate less dense tissue. For example, the darkest portion of coronal view 600 is indicative of spaces within brain 28 that contain cerebral spinal fluid (CSF). White portions of brain 28 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 6, lead 604 may be a lead icon that represents an actual lead implanted within patient 12. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located on the backside of lead 604. When electrical signals, such as LFP signals originate from target tissue 602, the largest amplitude and power of the signal will likely be sensed by the electrode or electrode combination closest to target tissue 602. In this example, a sensing electrode combination 606B and 608B may sense a larger amplitude electrical signal from target tissue 602 than any other electrode combinations on lead 604. If lead 604 moves with respect to target tissue 602, a different electrode, such as electrode 606A (for lead rotation) or electrode 608B (for longitudinal lead movement), may not sense electrical signals with the largest amplitude.

As discussed in FIG. 2, after delivering electrical stimulation configured to induce dyskinesia and determining dyskinesia is present in sensed electrical signals, processing circuitry 40 may compare one or more characteristics of the power spectrum of the sensed electrical signals to one or more characteristics of the saved power spectrum of a stimulation induced neural response from a prior time (e.g., hours, days, or months prior) saved in biomarkers 59. If the one or more characteristics of the power spectrums are substantially different, processing circuitry 40 may examine characteristics of the power spectrums from electrical stimulation sensed by all electrode combinations to find a power spectrum indicative of the strongest induced dyskinesia response. The strongest dyskinesia response may be the largest magnitude of a peak at a frequency less than the pulse frequency of the delivered electrical stimulation. If the electrode combination associated with the largest peak in the power spectrum is different from the original electrode combination having the largest peak in the power spectrum, then processing circuitry 40 may determine the lead has moved (e.g., rotated or shifted) in the direction from the original electrode combination to the newest electrode combination. Processing circuitry 40 may store the movement and notify a clinician upon the patient's next clinical visit. In some examples, processing circuitry 40 may suspend electrical stimulation and/or select a different electrode combination in response to determining that the lead has moved.

Leads, such as lead 604, may be offset from a signal-source, such as target tissue 602. Lead 604 may be offset from the signal-source (e.g., target tissue 602) so that electrodes 606A, 606B, 608A and 608B do not become saturated with sensed electrical signals from the signal-source. If electrodes 606A, 606B, 608A and 608B become saturated with electrical signals it becomes difficult to determine which electrode is measuring a stronger signal strength as each electrode is saturated with the sensed electrical signal. In examples of the present disclosure, target tissue 602 may be within the dorsolateral motor STN.

Figure 7:
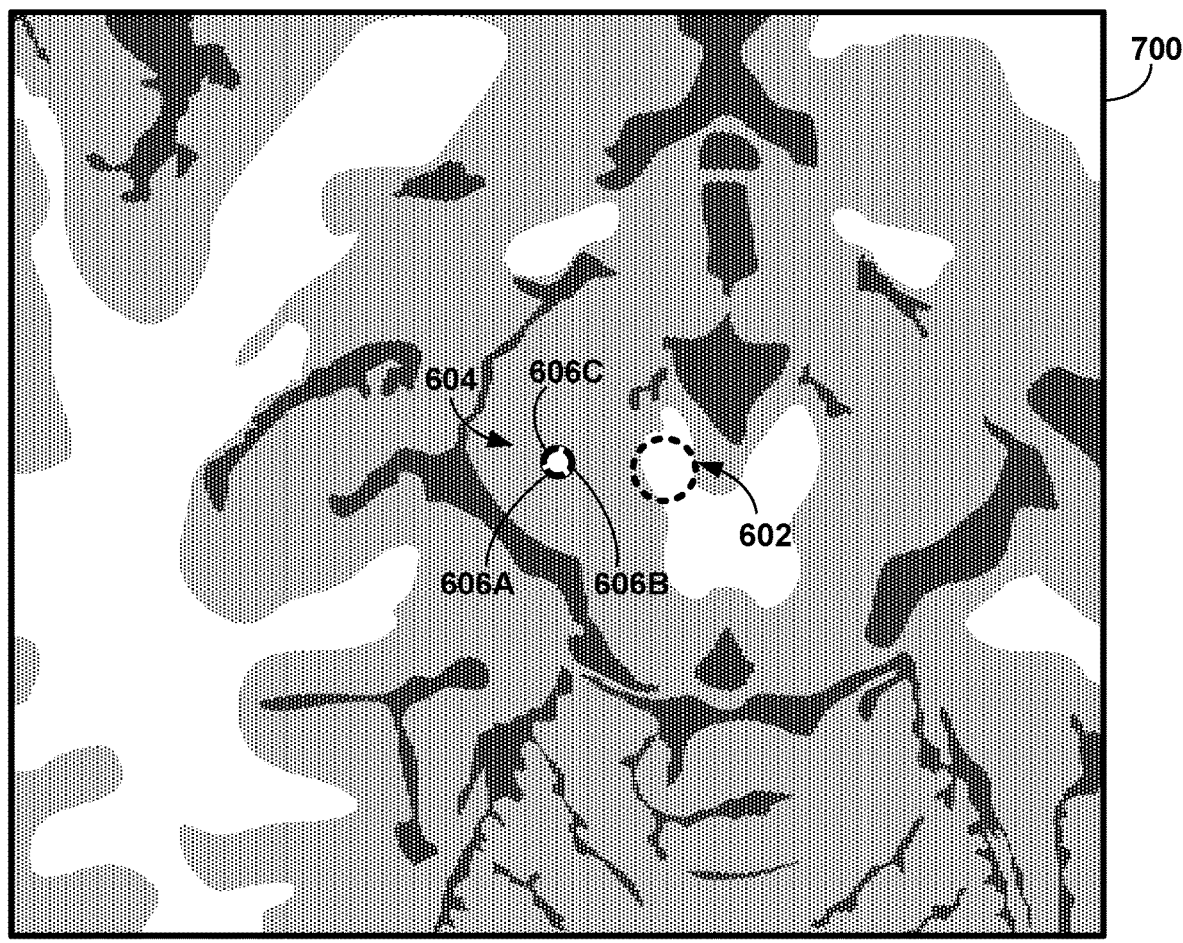
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude when compared to other electrodes. Although FIGS. 6 and 7 discuss electrical signals that may originate in tissue, the same spatial origin may be used when sensing electrical signals evoked from delivered stimulation or sensing delivered stimulation itself for determining lead movement.

Figure 8:
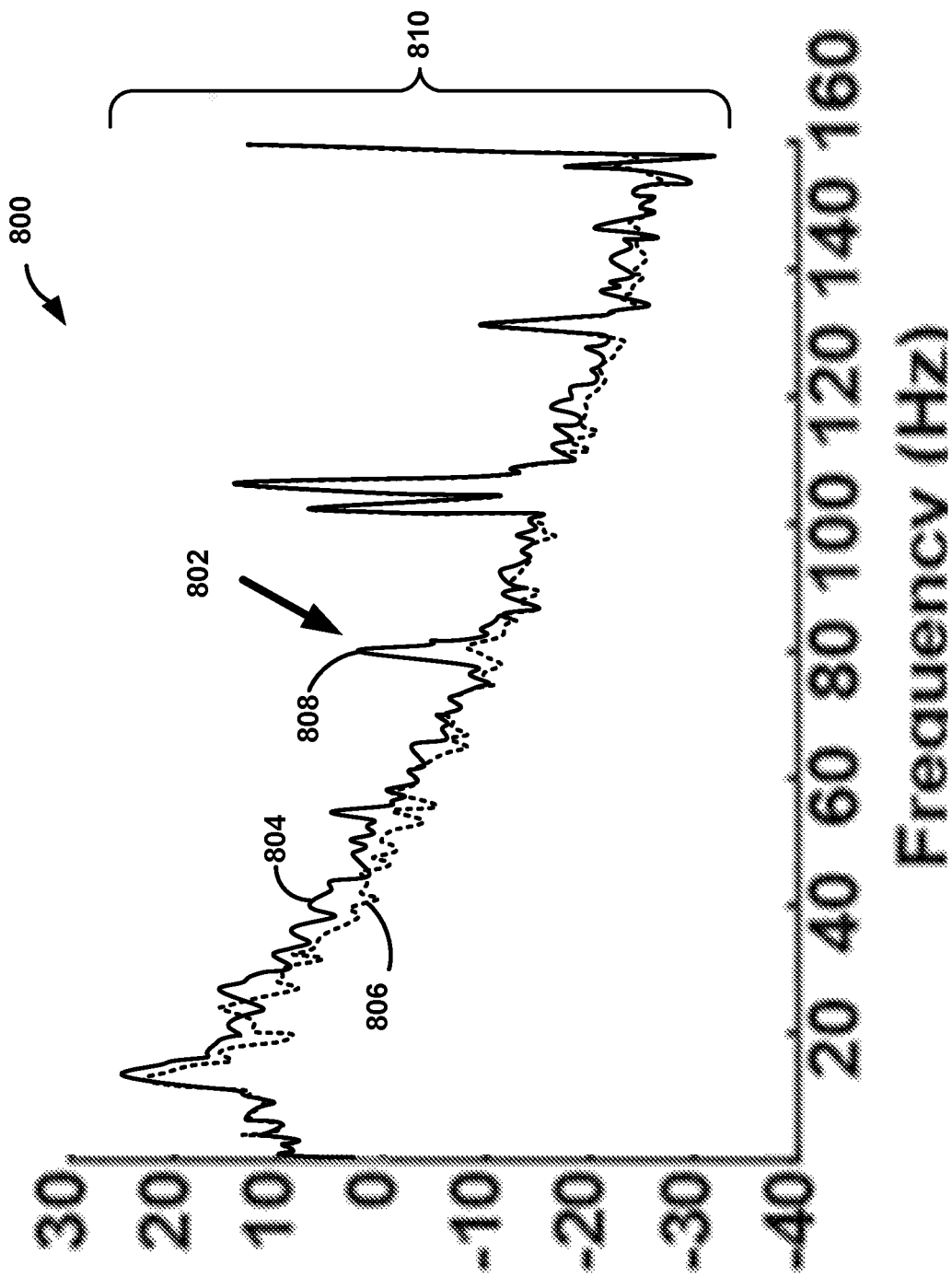
FIG. 8 is an example spectral power graph illustrating stimulation induced dyskinesia within LFPs sensed from a patient in accordance with techniques of the present disclosure.

FIG. 8 includes an example spectral power graph 800 illustrating peak 808 indicative of stimulation induced dyskinesia at time 802 within LFP 804 sensed from patient 12 in accordance with techniques of the present disclosure. In the example of FIG. 8, system 10 may have processing circuitry 40 configured to control implantable medical device 16 to deliver electrical stimulation at a first frequency to a portion (e.g., target tissue 602) of brain 28 of patient 12. As stated above, this stimulation frequency may be between approximately 20 Hz and approximately 500 Hz, such as between approximately 50 Hz and approximately 150 Hz, or approximately 130 Hz. The stimulation voltage may vary between approximately 0.1 volts and approximately 20 volts, such as between approximately 0.5 volts and approximately 10 volts, or approximately 5 volts. Processing circuitry 40 may vary the stimulation amplitude of delivered stimulation in order to induce dyskinesia. As discussed above, it may be desirable to find a stimulation amplitude that induces dyskinesia.

Stimulation configured to induce dyskinesia may be defined by a program stored on memory 42 and may be stored within therapy programs 54. IMD 16 may deliver stimulation over multiple electrode combinations and over a varying amplitude range while sensing electrical signals from different electrode combinations in order to detect the induced dyskinesia. The amplitude of the stimulation may be gradually increased until dyskinesia is discovered (i.e., peak 808 of LFP 804). Once dyskinesia is discovered, stimulation induced neural response program may be ceased so as to prevent further dyskinesia that may be unconformable for patient 12. Power spectrum 810 may be saved in biomarkers 59 for later reference as well as the electrode combination which sensed LFP 804.

In the example of FIG. 8, peak 808 indicative of stimulation induced dyskinesia may be observable in LFP 804. Stimulation induced dyskinesia is not a "natural state" normally found in brain 28, but it may be a normal feature of that can be induced in patients that have PD. Processing circuitry 40 may receive information representative of an electrical signal (e.g., LFPs 804 and 806) sensed from brain 28. In contrast to LFP 804, LFP 806 does not include a peak at time 802 because stimulation has not induced a peak indicative that dyskinesia was induced in the patient. Peak 808 may be shown in certain LFPs such as LFP 804, where the stimulation amplitude was above the dyskinesia threshold required to induce dyskinesia. Thus, there are features, not normally found in brain 28, but created or induced by stimulation therapy that may be used to provide improved stimulation therapy or to determine which electrode combinations are closest to regions that generate signals indicative of dyskinesia and/or determine that a lead has moved (e.g., rotated or shifted longitudinally).

Processing circuitry 40 may determine, from the information representative of the electrical signal, a peak 808 in a spectral power 810 of the electrical signal at a second frequency lower than the first frequency of the electrical stimulation. Peak 808 may occur at approximately 45% to 55% of the first stimulation frequency, which is approximately 130-160 Hz, when dyskinesia has been induced. Thus, peak 808 may be visualized, if induced, at a second frequency between 70 Hz to 80 Hz. Responsive to determining peak 808 in spectral power 810, represented in graph 800, of LFP 804 at the second frequency, processing circuitry 40 may perform an action. Additionally or alternatively, peak 808 may become apparent at harmonics or subharmonics of the delivered stimulation pulse frequency when dyskinesia has been induced. Additionally, oscillations of the delivered stimulation pulse frequency may occur in a high-frequency oscillation (HFO) range (e.g., >200 Hz).

In the example of FIG. 8, upon determination of peak 808, processing circuitry 40 may save power spectrum 810 and save the amplitude and the electrode combination that produced the power spectrum 810. Processing circuitry 40 may use the identified electrode combination to provide a therapy selected from therapy programs 54. Processing circuitry may create a dyskinesia tuning curve that places an upper threshold on amplitude used during stimulation therapy to prevent amplitudes that may induce dyskinesia during therapy. Additionally or alternatively, processing circuitry 40 may implement amplitude titration upon knowledge of which electrode combination received the strongest spectral power amplitude LFP and the amplitude of stimulation that induced dyskinesia 802. Additionally or alternatively, processing circuitry 40 may collect information that illuminates a neural state, measures a susceptibility to stimulation or therapy, and assess disease progression.

IMD 16 may deliver stimulation to evoke responses and determine appropriate parameters including electrode combinations and/or amplitude values that at least partially define subsequent stimulation therapy. Additionally, stimulation may be delivered to structures other than the STN to induce dyskinesia. Such stimulation induced neural response may also assist in reducing implantation and programming time as a clinician will be able to detect a target tissue with an automatic amplitude sweep or even manual sweep. Once the induced dyskinesia is identified, a clinician may then select the electrode combination that sensed the induced dyskinesia and identify an amplitude value, amplitude threshold, and/or amplitude range, for the programming of one or more initial stimulation programs. Such an automated or partially automated process may only take minutes as opposed to hours or days of trial and error parameter selection. Additionally or alternatively, stimulation induced neural response may be used to shape a stimulation therapy shape (e.g., monopolar, segmented or fractionalized). Simulation induced neural response may be used as a therapy toolbox item that other therapy programs may use to improve therapy programming.

Figure 9:
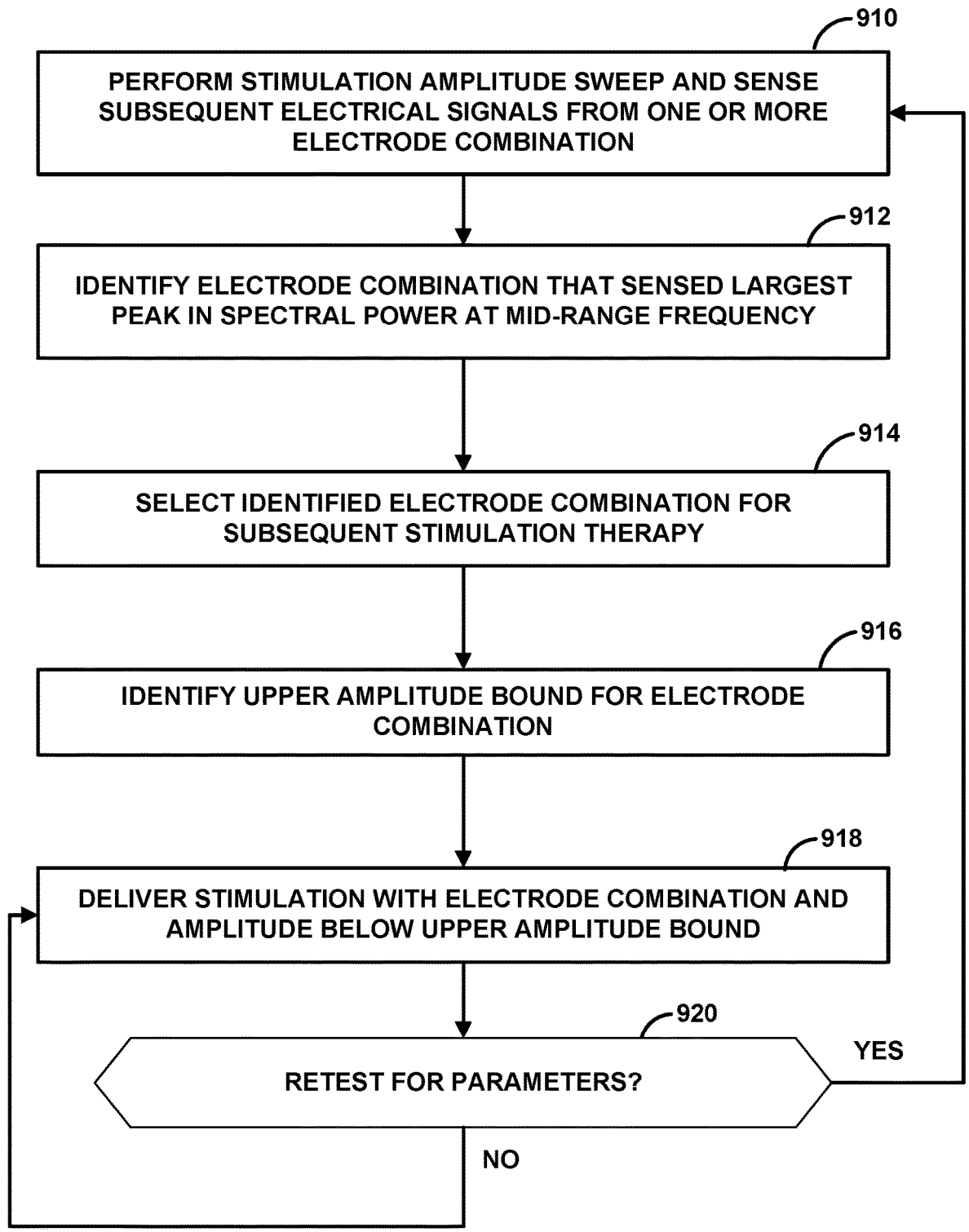
FIG. 9 is a flow diagram illustrating an example method of determining one or more parameter values that at least partially define electrical stimulation in accordance with various techniques of the present disclosure.

FIG. 9 is a flow diagram illustrating an example method of determining parameter values based on induced dyskinesia in accordance with techniques of the present disclosure. Processing circuitry 40 of IMD 16 will be described as performing the techniques of FIG. 9, but any other component, device, or combination of components and/or devices may perform these techniques in other examples. In the example of FIG. 9, processing circuitry 40 controls implantable medical device 16 to deliver electrical stimulation using an amplitude sweep and sense subsequent electrical signals from one or more stimulation electrode combinations (910).

The sweep of amplitude values may be automatically performed by processing circuitry 40 or it may be performed manually by a clinician during initial programming of IMD 16 during implantation. The stimulation may be delivered via a sweep of amplitudes for a single electrode combination or respective sweeps for multiple different electrode combinations. Alternatively, IMD 16 may deliver stimulation from multiple different electrode combinations at the same amplitude and then iteratively increase the amplitude for all electrode combinations to sweep through the different electrode combination. For delivering stimulation to different electrode combinations, IMD 16 may iteratively control independent current sources to deliver stimulation from or between different directional segments (e.g., different circumferential electrodes such as those shown in FIGS. 5B, 5C, and 5D) or across axial levels of electrodes axially positioned along the lead (e.g., between different combinations of axial electrodes 404A, 404B, 404C, and 404D in FIG. 4A). In this manner, different stimulation electrode combinations may be evaluated to determine which electrode combinations provide stimulation that induces dyskinesia. In an automatic sweep, processing circuitry 40 may increase pulse amplitudes at 0.1 mA increments through a predetermined range of amplitudes. In other examples, processing circuitry 40 may perform the automatic sweep by increasing pulse amplitudes at predetermined increments until processing circuitry 40 determines that dyskinesia has been induced and subsequently terminating stimulation. At designated periods of time that are most convenient to patient 12 (e.g., such as when patient 12 is sleeping, relaxing, or in response to unusual patient symptoms or side effects), processing circuitry may perform the amplitude stimulation sweep over one or more electrode combinations. The stimulation may be performed over an automatic sweep of amplitude values in search of an amplitude that induces dyskinesia.

In some examples, processing circuitry 40 may determine a time to perform the respective sweep of the range of amplitude values. Processing circuitry 40 may control implantable medical device 16 to deliver the electrical stimulation according to the sweep of the range of amplitude values at the determined time. Patient 12 may select the determined time, or a clinician may set the time upon implantation or the time may be preset in values stored in memory 42. Further, the stimulation induced neural response sweep time may be adjustable by patient 12, at programmer 70, to occur at a time that is the most convenient for patient 12 (e.g., when patient 12 is sleeping).

Processing circuitry 40 may analyze sensed electrical signals for one or more characteristic indicating that dyskinesia was induced. In some examples, IMD 16 may sense electrical signals via multiple different electrode combination after delivering stimulation from a single electrode combination. In other examples, IMD 16 may sense electrical signals via a single electrode combination after delivering stimulation from one or more electrode combinations. For example, processing circuitry may search for and identify any peaks at a mid-range frequency in the spectral power of sensed electrical signals and identify the electrode combination that sensed the largest such peak (912). For example, processing circuitry 40 may identify the electrode combination that sensed peak 808 in spectral power 810 of LFP 804 at the second frequency. Alternatively, processing circuitry 40 may identify the electrode combination that delivered the stimulation that induced peak 808 in spectral power 810 of LFP 804 at the second frequency. Processing circuitry 40 may then select this identified electrode combination for delivering subsequent stimulation therapy (914). Processing circuitry 40 may then set an upper amplitude bound at an amplitude value less than an amplitude of electrical stimulation that induced peak 808 in spectral power 810 indicative of stimulation induced dyskinesia (916). The upper amplitude bound limits amplitude of subsequent electrical stimulation delivered to brain 28 so dyskinesia is not induced during the normal course of stimulation therapy. In some examples, IMD 16 may vary stimulation amplitude below this upper amplitude bound based on other feedback signals or the clinician may set the appropriate amplitude to a value below the upper amplitude bound. Thus, by knowing the amplitude which induces dyskinesia 802, processing circuitry 40 can set an upper bound to reduce the likelihood that subsequent stimulation therapy could inadvertently induce dyskinesia.

Peak 808 in spectral power 810 of the electrical signal may occur at a harmonic or a subharmonic frequency (e.g., which may be within a range from about 45 percent to about 55 percent) of the stimulation frequency (e.g., between 70 Hz to 80 Hz for delivered pulses of a frequency of between 130 Hz and 180 Hz). A magnitude of peak 808 in spectral power 810 at the second frequency may be an order of magnitude greater than the power at adjacent frequencies. Additionally or alternatively, peak 808 may be significantly or detectably greater than the power at adjacent frequencies. However, peak 808 may be identified by other methods that identify a power greater than variations at adjacent frequencies. Thus, processing circuitry 40 may be able to discern peak 808 from other smaller power variations at other frequencies. IMD 16 may then be controlled to deliver stimulation with the identified electrode combination and amplitude below the upper amplitude bound (918).

If processing circuitry 40 determines that the system should retest for different parameters ("YES" branch of block 920), processing circuitry may again perform the stimulation amplitude sweep (910). Example situations that could trigger the retest may include a predetermined schedule, time from the last test, sensors indicating patient symptoms no longer being suppressed by delivered stimulation, or patient requested retest. If processing circuitry 40 determines that no retest is necessary ("NO" branch of block 920), processing circuitry 40 may continue to deliver stimulation with the current parameter vales (918).

In some examples, processing circuitry 40 may determine, during a retest, that a different electrode combination now is associated with the largest peak in the spectral power indicative of the induced dyskinesia. Processing circuitry 40 may responsively determine that the lead carrying electrodes of the different electrode combination has rotated or otherwise moved (based on the previously used electrode combination). Processing circuitry 40 may detect this lead rotation and modify one or more parameter values without any need to contact a clinician for new programming of therapy. In other examples, processing circuitry 40 may suspend therapy and notify the patient and/or clinician of the lead rotation. Processing circuitry 40 may prevent further stimulation until new parameter values are selected or confirmed by the patient and/or clinician.

In this manner, processing circuitry 40 may receive subsequent information representative of respective electrical signals sensed by the first electrode combination and a second electrode combination. Processing circuitry 40 may determine, from the information representative of the respective electrical signals, that the second electrode combination sensed peak of the spectral power having a greater magnitude than a peak of spectral power sensed by the first electrode combination. Based on this detection, processing circuitry 40 controls medical device 16 to deliver subsequent electrical stimulation via the second electrode combination instead of the first electrode combination.

Processing circuitry 40 may adjust, based on determination of peak 808 in spectral power 810, at least one therapy parameter that at least partially defines subsequent electrical stimulation deliverable to patient 12. This parameter may be a different electrode combination based upon a sensed peak higher than the former electrode combination. The parameter may be a new amplitude for stimulation based upon an amplitude which induced dyskinesia during the last automatic dyskinesia amplitude sweep.

Processing circuitry 40 may also select a new electrode combination based upon the complete absence of a peak in the spectral power. For example, if processing circuitry 40 receives an electrical signal sensed by the electrode combination and determines an absence of a peak in a spectral power of the electrical signal. Processing circuitry 40 may initiate another stimulation induced neural response to discover dyskinesia and select a new electrode combination different than the first electrode combination for subsequent electrical stimulation.

Processing circuitry 40 may also output, for display, a representation of peak 808 in spectral power 810 of LFP 804 at user interface 76 as well as an indication of an electrode combination that sensed peak 808. Although described as being carried out within IMD 16, one or more of the steps may be completed by programmer 70.

Figure 10:
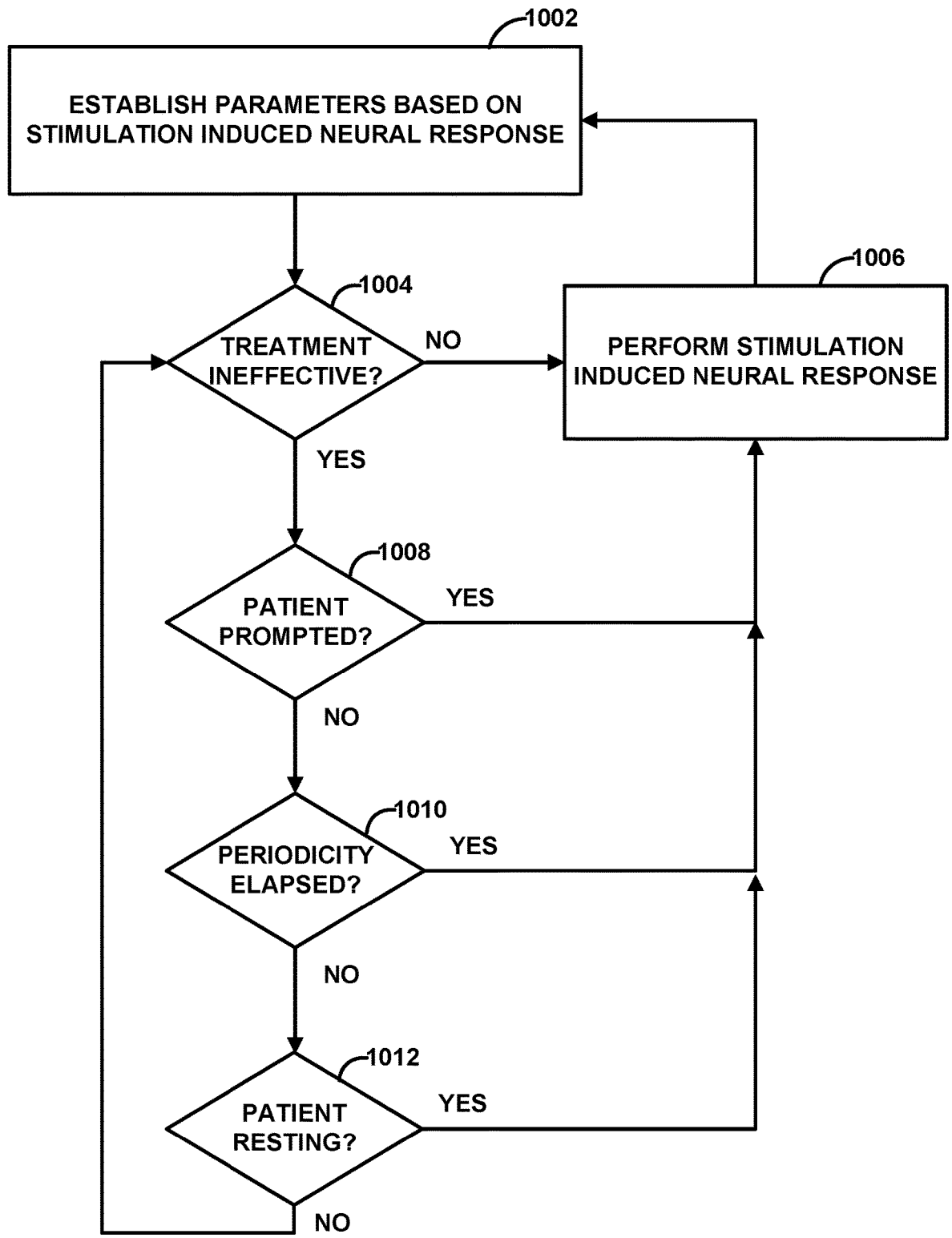
FIG. 10 is a flow diagram illustrating an example method of determining when to initiate a stimulation induced neural response for parameter value selection in accordance with various techniques of the present disclosure.

FIG. 10 is a flow diagram illustrating an example method of determining when to initiate a stimulation induced neural response for parameter selection in accordance with techniques of the present disclosure. Processing circuitry 40 of IMD 16 will be described as performing the techniques of FIG. 10, but any other component, device (such as programmer 14), or combination of components and/or devices may perform these techniques in other examples. In the example of FIG. 10, stimulation parameters are based on stimulation induced neural response (e.g., dyskinesia) (1002). As discussed in example FIG. 9, electrode combinations may be selected based upon the electrode combination that provides a spectral power providing a representation of LFPs from target tissue 602. Further, upon detection of peak 808, processing circuitry 40 may provide for amplitude titration of stimulation amplitude to ensure patient 12 receives therapy, but not side effects such as dyskinesia.

In the example of FIG. 10, there are many situations that may cause processing circuitry 40 to initiate an induced neural response to determine if current stimulation parameters need to be modified. For example, processing circuitry 40 may communicate with programmer 70 to initiate a question to patient 12 inquiring whether the current treatment is effective or not (1004). If patient 12 provides input that the current stimulation therapy is not effective ("NO" branch of block 1004), then a stimulation induced neural response may be initiated and processing circuitry 40 may retest for induced dyskinesia (1006).

If patient 12 submits input indicating that the stimulation therapy is effective ("YES" branch of block 1004), processing circuitry 40 may determine if patient 12 has requested a stimulation induced neural response (1008). If patient 12 has requested a stimulation induced neural response ("YES" branch of block 1008), then processing circuitry 40 may initiate another retest using the stimulation induced neural response (1006). If patient 12 has not requested a stimulation induced neural response, ("NO" branch of block 1008) processing circuitry 40 determines whether a periodicity limit has elapsed (1010).

An automatic sweep for simulation induced neural response may be set to occur periodically so that therapy programming may be determined to be effective. The periodicity may be set by a clinician (e.g., every 24 hours, every week, every month, etc.) or IMD 16 may be preprogrammed with a preset trigger event (e.g., detecting patient 12 lying down or resting). If processing circuitry 40 determines the periodicity set has elapsed ("YES" branch of block 1010), processing circuitry 40 initiates another stimulation induced neural response (1006). If processing circuitry 40 determines the periodicity set has not elapsed ("NO" branch of block 1010), processing circuitry may determine if patient 12 is resting (1012). For example, processing circuitry 40 may determine that patient 12 is resting if patient 12 has been lying down for over a predetermined period of time. If patient 12 is resting (e.g., sleeping) ("YES" branch of block 1012), processing circuitry 40 performs a stimulation induced neural response (1006). If patient 12 is not resting ("NO" branch of block 1012), processing circuitry 40 returns to determine if the current stimulation treatment is effective or not (1004). The example triggers for retesting for appropriate stimulation parameter of FIG. 10 may be different in other examples. For example, processing circuitry 40 may employ fewer or greater number of possible triggers.

Figure 11:
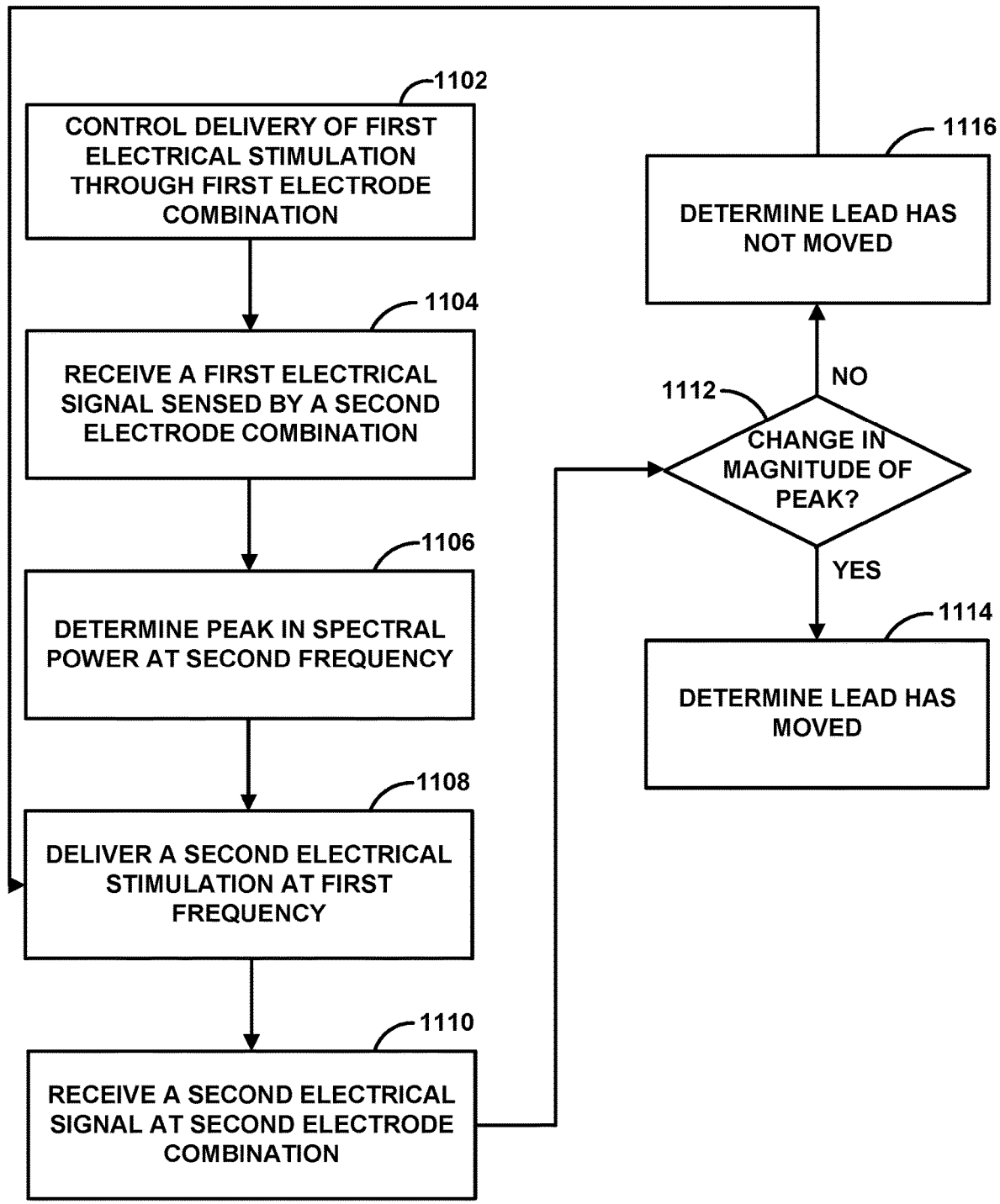
FIG. 11 is a flow diagram illustrating an example method of determining lead movement in accordance with various techniques of the present disclosure.

FIG. 11 is a flow diagram illustrating an example method of determining lead movement in accordance with techniques of the present disclosure. Processing circuitry 40 of IMD 16 will be described as performing the techniques of FIG. 11, but any other component, device, or combination of components and/or devices may perform these techniques in other examples. In the example of FIG. 11, processing circuitry 40 controls medical device 16 to deliver a first electrical stimulation at a first frequency to brain 28 of patient 12 via a first electrode combination (1102). The first electrode combination may be set at implantation by a clinician or an electrode combination determined on the last occurring stimulation induced neural response. Medical leads may move or otherwise rotate after implantation in a patient. The example of FIG. 11 enables medical device 16 to identify lead movement through the detection of dyskinesia through the stimulation induced neural response procedure performed at different times. Once movement of the lead is detected, processing circuitry 40 may suspend current therapy, change therapy, change electrode combination for stimulation, or some combination thereof.

Processing circuitry 40 receives information representative of a first electrical signal (e.g., LFPs) sensed by a second electrode combination of a medical lead from brain 28 after delivery of the first electrical stimulation (1104). Processing circuitry 40 then determines from the LFPs of the first electrical signal, a peak in a spectral power of the first electrical signal at a second frequency lower than the first frequency of the first electrical stimulation (1106). For example, induced dyskinesia may manifest as a peak over base amplitude at a frequency about half the pulse frequency of the delivered stimulation. At a later time to check for lead movement, medical device 16 may be controlled by processing circuitry to deliver a second electrical stimulation at the first frequency to the brain of the patient via the first electrode combination (1108). Processing circuitry receives a second electrical signal (e.g., LFPs) sensed by the second electrode combination from the brain after delivery of the second electrical stimulation (1110). From the LFPs of the second electrical signal, processing circuitry 40 determines whether there is a change in the magnitude of the peak in a spectral power of the second electrical signal at the second frequency (1112). For example, processing circuitry 40 may determine that the magnitude of the peak has changed when the difference between the magnitude of the peak of the first signal and the magnitude of the peak of the second signal exceeds a threshold difference. The threshold difference may be a percentage of the magnitude of the first peak or an absolute magnitude value. In other examples, machine-learning based methods of detecting change may be used. Additionally or alternatively, other machine-learning based methods may determine the probability that second peak is lower (e.g. using Bayesian-related methods or other machine learning techniques). In another example, processing circuitry 40 may classify the second peak as being different if there is a statistical variance between the first and second peak, such as in different forms of neural networks or fuzzy methods.

Responsive to determining that there is change in the magnitude of the peak in the spectral power of the second electrical signal at the second frequency ("YES" branch of block 1112), processing circuitry 40 determines that the medical lead has moved (e.g., longitudinally or rotated) with respect to the brain of the patient (1114). If processing circuitry 40 determines that there is no change in the magnitudes of the peaks of the first and second electrical signals ("NO" branch of block 112), processing circuitry 40 may determine that the lead has not moved and maintain current stimulation therapy (1116). Additionally or alternatively, processing circuitry 40 may return to block 1108 iteratively to deliver a third, fourth up to an nth ("n" being a positive whole number) stimulation until dyskinesia is detected. Further, a third, fourth and up to nth receiving electrode combination may sense the LFPs from the stimulation signals. Thus, processing circuitry 40 may be making multiple comparisons from many electrode combinations to decide if a change in magnitude of peak (1112) has occurred.

Processing circuitry 40 may determine whether the lead has shifted longitudinally or moved based on the difference between the electrode combinations associated with the prior largest peak and the recent largest peak in the spectral power. For example, if the prior and recent electrode combinations are just located at different circumferential positions around the lead, processing circuitry 40 may determine that the lead has moved. If the prior and recent electrode combinations are located at different longitudinal positions along the length of the lead, processing circuitry 40 may determine that the lead has shifted longitudinally.

This disclosure includes various examples, such as the following examples. Example 1: a method comprising: controlling, by processing circuitry, a medical device to deliver electrical stimulation at a first frequency to a portion of a brain of a patient; receiving, by the processing circuitry, information representative of an electrical signal sensed from the brain after delivery of the electrical stimulation; determining, by the processing circuitry and from the information representative of the electrical signal, a peak in a spectral power of the electrical signal at a second frequency lower than the first frequency of the electrical stimulation; and responsive to determining the peak in the spectral power of the electrical signal at the second frequency, performing, by the processing circuitry, an action.

Example 2: the method of claim 1, wherein controlling the medical device to deliver electrical stimulation comprises controlling the medical device to perform, for a plurality of electrode combinations, a respective sweep of a range of amplitude values; and determining the peak in the spectral power comprises determining, for at least one electrode combination of the plurality of electrode combinations, the peak in the spectral power of the electrical signal at the second frequency for the respective electrode combination of the plurality of electrode combinations.

Example 3: the method of example 2, further comprising determining a time to perform the respective sweep of the range of amplitude values; and controlling the medical device to deliver the electrical stimulation according to the sweep of the range of amplitude values at the determined time.

Example 4: the method of any of examples 1 through 3, further comprising setting an upper amplitude bound at an amplitude value less than an amplitude of electrical stimulation that elicits the peak in the spectral power, the peak indicative of stimulation induced dyskinesia, wherein the upper amplitude bound limits amplitude of subsequent electrical stimulation delivered to the brain.

Example 5: the method of any of examples 1 through 4, wherein the peak in a spectral power of the electrical signal is at one or a harmonic or a subharmonic frequency of the stimulation frequency.

Example 6: the method of any of examples 1 through 5, wherein a magnitude of the peak in spectral power at the second frequency is an order of magnitude greater than the power at adjacent frequencies.

Example 7: the method of any of examples 1 through 6, further comprising determining, by the processing circuitry and from the information representative of the electrical signal, an electrode combination that sensed the peak in the spectral power, and wherein the peak in the spectral power sensed by the electrode combination is greater in magnitude than any other peak in spectral power sensed by other electrode combinations of a plurality of electrode combinations.

Example 8: the method of example 7, wherein performing the action comprises controlling, by processing circuitry, the medical device to deliver electrical stimulation to the brain of the patient via the electrode combination that sensed the peak in the spectral power.

Example 9: the method of any of examples 7 or 8, wherein the electrode combination is a first electrode combination, and wherein the method further comprises: receiving subsequent information representative of respective electrical signals sensed by the first electrode combination and a second electrode combination different than the first electrode combination; determining, from the information representative of the respective electrical signals, that the second electrode combination sensed a peak of spectral power having a greater magnitude than a peak of spectral power sensed by the first electrode combination; and controlling the medical device to deliver subsequent electrical stimulation via the second electrode combination instead of the first electrode combination.

Example 10: the method of any of examples 1 through 9, further comprising determining, by the processing circuitry and based on the peak in spectral power, that the electrical simulation induced dyskinesia in the patient.

Example 11: the method of any of examples 1 through 10, further comprising adjusting, by the processing circuitry and based on determination of the peak in spectral power, at least one therapy parameter that at least partially defines subsequent electrical stimulation deliverable to the patient.

Example 12: the method of any of examples 1 through 11, wherein the electrical signal is sensed by a first electrode combination and the information comprises first information, and wherein the method further comprises: receiving second information representative of a second electrical signal sensed by the electrode combination; determining, from the second information, an absence of a peak in a spectral power of the second electrical signal at the second frequency; and selecting a second electrode combination different than the first electrode combination for subsequent electrical stimulation.

Example 13: the method of any of examples 1 through 12, wherein performing the action comprises outputting, for display, a representation of the peak in the spectral power of the electrical signal at the second frequency and an indication of an electrode combination that sensed the electrical signal.

Example 14: A system comprising processing circuitry configured to: control a medical device to deliver electrical stimulation at a first frequency to a portion of a brain of a patient; receive information representative of an electrical signal sensed from the brain after delivery of the electrical stimulation; determine, from the information representative of the electrical signal, a peak in a spectral power of the electrical signal at a second frequency lower than the first frequency of the electrical stimulation; and responsive to determining the peak in the spectral power of the electrical signal at the second frequency, perform an action.

Example 15: the system of example 14, wherein the processing circuitry is configured to: control the medical device to deliver electrical stimulation by controlling the medical device to perform, for a plurality of electrode combinations, a respective sweep of a range of amplitude values; and determine the peak in the spectral power by determining, for at least one electrode combination of the plurality of electrode combinations, the peak in the spectral power of the electrical signal at the second frequency for the respective electrode combination of the plurality of electrode combinations.

Example 16: the system of example 15, wherein the processing circuitry is further configured to: determine a time to perform the respective sweep of the range of amplitude values; and control the medical device to deliver the electrical stimulation according to the sweep of the range of amplitude values at the determined time.

Example 17: the system of any of examples 14 through 16, wherein the processing circuitry is further configured to set an upper amplitude bound at an amplitude value less than an amplitude of electrical stimulation that elicits the peak in the spectral power, the peak indicative of stimulation induced dyskinesia, wherein the upper amplitude bound limits amplitude of subsequent electrical stimulation delivered to the brain.

Example 18: the system of any of examples 14 through 17, wherein the peak in a spectral power of the electrical signal is at one of a harmonic or a subharmonic frequency of the stimulation frequency.

Example 19: the system of any of examples 14 through 18, wherein a magnitude of the peak in spectral power at the second frequency is an order of magnitude greater than the power at adjacent frequencies.

Example 20: the system of any of examples 14 through 19, wherein the processing circuitry is further configured to determine from the information representative of the electrical signal, an electrode combination that sensed the peak in the spectral power, and wherein the peak in the spectral power sensed by the electrode combination is greater in magnitude than any other peak in spectral power sensed by other electrode combinations of a plurality of electrode combinations.

Example 21: the system of example 20, wherein the processing circuitry is configured to perform the action by controlling the medical device to deliver electrical stimulation to the brain of the patient via the electrode combination that sensed the peak in the spectral power.

Example 22: the system of any of examples 20 through 21, wherein the electrode combination is a first electrode combination, and wherein the processing circuitry is configured to: receive subsequent information representative of respective electrical signals sensed by the first electrode combination and a second electrode combination different than the first electrode combination; determine, from the information representative of the respective electrical signals, that the second electrode combination sensed a peak of spectral power having a greater magnitude than a peak of spectral power sensed by the first electrode combination; and control the medical device to deliver subsequent electrical stimulation via the second electrode combination instead of the first electrode combination.

Example 23: the system of any of examples 14 through 22, wherein the processing circuitry is further configured to determine, based on the peak in spectral power, that the electrical simulation induced dyskinesia in the patient.

Example 24: the system of any of examples 14 through 23, wherein the processing circuitry is further configured to adjust, based on determination of the peak in spectral power, at least one therapy parameter that at least partially defines subsequent electrical stimulation deliverable to the patient.

Example 25: the system of any of examples 14 through 24, wherein the electrical signal is sensed by a first electrode combination and the information comprises first information, and wherein the processing circuitry is further configured to: receive second information representative of a second electrical signal sensed by the electrode combination; determine, from the second information, an absence of a peak in a spectral power of the second electrical signal at the second frequency; and select a second electrode combination different than the first electrode combination for subsequent electrical stimulation.

Example 26: the system of examples 14 through 25, wherein the processing circuitry is configured to perform the action by outputting, for display, a representation of the peak in the spectral power of the electrical signal at the second frequency and an indication of an electrode combination that sensed the electrical signal.

Example 27: a computer readable medium comprising instructions that, when executed, cause processing circuitry to: control a medical device to deliver electrical stimulation at a first frequency to a portion of a brain of a patient; receive information representative of an electrical signal sensed from the brain after delivery of the electrical stimulation; determine from the information representative of the electrical signal, a peak in a spectral power of the electrical signal at a second frequency lower than the first frequency of the electrical stimulation; determine based on the peak in spectral power, that the electrical simulation induced dyskinesia in the patient; determine from the information representative of the electrical signal, an electrode combination that sensed the peak in the spectral power, and wherein the peak in the spectral power sensed by the electrode combination is greater in magnitude than any other peak in spectral power sensed by other electrode combinations of a plurality of electrode combinations; and adjust based on determination of the peak in spectral power, at least one therapy parameter that at least partially defines subsequent electrical stimulation deliverable to the patient.

Example 101: a method comprising: controlling, by processing circuitry, a medical device to deliver a first electrical stimulation at a first frequency to a brain of a patient via a first electrode combination; receiving, by the processing circuitry, information representative of a first electrical signal sensed by a second electrode combination of a medical lead from the brain after delivery of the first electrical stimulation; determining, by the processing circuitry and from the information representative of the first electrical signal, a peak in a spectral power of the first electrical signal at a second frequency lower than the first frequency of the first electrical stimulation; controlling, by the processing circuitry, the medical device to deliver a second electrical stimulation at the first frequency to the brain of the patient via the first electrode combination; receiving, by the processing circuitry, information representative of a second electrical signal sensed by the second electrode combination from the brain after delivery of the second electrical stimulation; determining, by the processing circuitry and from the information representative of the second electrical signal, a change in a magnitude of the peak in a spectral power of the second electrical signal at the second frequency; and responsive to determining the change in the magnitude of the peak in the spectral power of the second electrical signal at the second frequency, determining, by the processing circuitry and based on the change, that the medical lead has moved with respect to the brain of the patient.

Example 102: the method of example 101, wherein the peak in the spectral power is a first peak in the spectral power, and wherein determining the change in the magnitude of the first peak in the spectral power comprises determining that a magnitude of a second peak in the spectral power of the second electrical signal at the second frequency is lower than the magnitude of the first peak.

Example 103: the method of any of examples 101 through 102, wherein the magnitude of the second peak is lower by a threshold difference than the magnitude of the first peak.

Example 104: the method of any of examples 101 through 103, wherein the peak in the spectral power is a first peak in the spectral power, and wherein the method further comprises: receiving information representative of a third electrical signal sensed by a third electrode combination from the brain after delivery of the second electrical stimulation; determining, by the processing circuitry and from the information representative of the third electrical signal, a second peak in a spectral power of the third electrical signal; and determining, by the processing circuitry, that a magnitude of the second peak is within a threshold difference of the magnitude of the first peak, wherein determining that the medical lead has moved comprises determining that the third electrode combination moved to a previous position of the second electrode combination.

Example 105: the method of example 104, further comprising controlling, by the processing circuitry, the medical device to deliver electrical stimulation therapy via the third electrode combination.

Example 106: the method of any of examples 101 through 105, further comprising: receiving information representative of electrical signals sensed by respective electrode combinations of a plurality of electrode combinations from the brain after delivery of the second electrical stimulation; determining, by the processing circuitry and from the information representative of the respective electrical signals, that no peaks are present in spectral powers of any of the respective electrical signals at the second frequency; and determining, by the processing circuitry, that the medial lead has a lead integrity issue.

Example 107: the method of any of examples 101 through 106, further comprising: receiving information representative of electrical signals sensed by respective electrode combinations of a plurality of electrode combinations from the brain after delivery of the second electrical stimulation; determining, by the processing circuitry and from the information representative of the respective electrical signals, that no peaks are present in spectral powers of any of the respective electrical signals at the second frequency; and determining, by the processing circuitry, that the medial lead has a lead integrity issue.

Example 108: the method of example 107, further comprising outputting, for display, an alert notification indicative of the lead integrity issue.

Example 109: the method of any of examples 107 through 108, responsive to determining that the medical lead has the lead integrity issue, suspending delivery of electrical stimulation therapy via the medical lead.

Example 110: the method of any of examples 107 through 109, further comprising, responsive to determining that the medical lead has the lead integrity issue, performing a lead integrity check on the medical lead.

Example 111: the method of any of examples 101 through 110, wherein determining the change in the magnitude of the peak in the spectral power comprises determining that the peak is no longer present at the second frequency of the second electrical signal.

Example 112: the method of any of examples 101 through 111, further comprising adjusting, based on the rotation of the medical lead, a value of at least one stimulation parameter that at least partially defines electrical stimulation to be delivered to the brain of the patient.

Example 113: the method of example 112, wherein adjusting the value of the at least one stimulation parameter comprises selecting a different electrode combination for delivering the electrical stimulation to be delivered to the brain of the patient.

Example 114: the method of example 113, wherein selecting the different electrode combination comprises: determining that a largest peak in spectral power at the second frequency from respective electrical signals from a plurality of electrode combinations is associated with the different electrode combination; and selecting the different electrode combination for delivering the electrical stimulation to be delivered to the brain of the patient Example 115: the method of any of examples 101 through 114, wherein the peak in the spectral power represents stimulation induced dyskinesia in the patient.

Example 116: a system comprising processing circuitry configured to: control a medical device to deliver a first electrical stimulation at a first frequency to a brain of a patient via a first electrode combination; receive information representative of a first electrical signal sensed by a second electrode combination of a medical lead from the brain after delivery of the first electrical stimulation; determine, from the information representative of the first electrical signal, a peak in a spectral power of the first electrical signal at a second frequency lower than the first frequency of the first electrical stimulation; control the medical device to deliver a second electrical stimulation at the first frequency to the brain of the patient via the first electrode combination; receive information representative of a second electrical signal sensed by the second electrode combination from the brain after delivery of the second electrical stimulation; determine, from the information representative of the second electrical signal, a change in a magnitude of the peak in a spectral power of the second electrical signal at the second frequency; and responsive to determining the change in the magnitude of the peak in the spectral power of the second electrical signal at the second frequency, determine, based on the change, that the medical lead has moved with respect to the brain of the patient.

Example 117: the system of example 116, wherein the peak in the spectral power is a first peak in the spectral power, and wherein determining the change in the magnitude of the first peak in the spectral power comprises the processing circuitry to determine that a magnitude of a second peak in the spectral power of the second electrical signal at the second frequency is lower than the magnitude of the first peak.

Example 118: the system of example 117, wherein the magnitude of the second peak is lower by a threshold different than the magnitude of the first peak.

Example 119: the system of any of examples 116 through 118, wherein the peak in the spectral power is a first peak in the spectral power, and wherein the processing circuitry is further configured to: receive information representative of a third electrical signal sensed by a third electrode combination from the brain after delivery of the second electrical stimulation; determine, from the information representative of the third electrical signal, a second peak in a spectral power of the third electrical signal; and determine that a magnitude of the second peak is within a threshold difference of the magnitude of the first peak, wherein determining that the medical lead has moved comprises determining that the third electrode combination moved to a previous position of the second electrode combination.

Example 120: the system of any of examples 116 through 119, wherein the processing circuitry is further configured to control the medical device to deliver electrical stimulation therapy via the third electrode combination.

Example 121: the system of any of examples 116 through 120, wherein the processing circuitry is further configured to: receive information representative of electrical signals sensed by respective electrode combinations of a plurality of electrode combinations from the brain after delivery of the second electrical stimulation; determine, from the information representative of the respective electrical signals, that no peaks are present in spectral powers of any of the respective electrical signals at the second frequency; and determine that the medial lead has a lead integrity issue.

Example 122: the system of example 121, wherein the processing circuitry is further configured to output, for display, an alert notification indicative of the lead integrity issue.

Example 123: the system of any of examples 121 through 122, wherein the processing circuitry is configured to, responsive to determining that the medical lead has the lead integrity issue, suspend delivery of electrical stimulation therapy via the medical lead.

Example 124: the system of any of examples 121 through 123, wherein the processing circuitry is configured to, responsive to determining that the medical lead has the lead integrity issue, perform a lead integrity check on the medical lead.

Example 125: the system of any of examples 116 through 124, wherein the processing circuitry is configured to determine the change in the magnitude of the peak in the spectral power by determining that the peak is no longer present at the second frequency of the second electrical signal.

Example 126: the system of any of examples 116 through 125, wherein the processing circuitry is further configured to adjust, based on the rotation of the medical lead, a value of at least one stimulation parameter that at least partially defines electrical stimulation to be delivered to the brain of the patient.

Example 127: the system of example 126, wherein the processing circuitry is configured to adjust the value of the at least one stimulation parameter by selecting a different electrode combination for delivering the electrical stimulation to be delivered to the brain of the patient.

Example 128: the system of any of examples 126 through 127, wherein the processing circuitry is configured to select the different electrode combination by: determining that a largest peak in spectral power at the second frequency from respective electrical signals from a plurality of electrode combinations is associated with the different electrode combination; and selecting the different electrode combination for delivering the electrical stimulation to be delivered to the brain of the patient.

Example 129: the system of any of examples 116 through 128, wherein the peak in the spectral power represents stimulation induced dyskinesia in the patient.

Example 130: the system of any of examples 116 through 129, further comprising the medical device, and wherein the medical device comprises an implantable medical device that houses the processing circuitry.

Example 131: a computer-readable medium comprising instructions that, when executed, cause processing circuitry to: control a medical device to deliver a first electrical stimulation at a first frequency to a brain of a patient via a first electrode combination; receive information representative of a first electrical signal sensed by a second electrode combination of a medical lead from the brain after delivery of the first electrical stimulation; determine, from the information representative of the first electrical signal, a peak in a spectral power of the first electrical signal at a second frequency lower than the first frequency of the first electrical stimulation; control the medical device to deliver a second electrical stimulation at the first frequency to the brain of the patient via the first electrode combination; receive information representative of a second electrical signal sensed by the second electrode combination from the brain after delivery of the second electrical stimulation; determine, from the information representative of the second electrical signal, a change in a magnitude of the peak in a spectral power of the second electrical signal at the second frequency; and responsive to determining the change in the magnitude of the peak in the spectral power of the second electrical signal at the second frequency, determine, based on the change, that the medical lead has moved with respect to the brain of the patient.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media. Various examples consistent with this disclosure have been described. These and other examples are within the scope of the following claims.

What is claimed is:

1. A method comprising:
controlling, by processing circuitry, a medical device to deliver electrical stimulation from a stimulation electrode combination and at a first frequency to a brain of a patient;
receiving, by the processing circuitry, information representative of a plurality of electrical signals sensed by a plurality of electrode combinations and induced by the electrical stimulation delivered from the stimulation electrode combination, wherein each electrical signal of the plurality of electrical signals are sensed by a respective electrode combination of the plurality of electrode combinations;
determining, by the processing circuitry and from the information representative of the plurality of electrical signals, a peak in a spectral power of the electrical signals at a second frequency lower than the first frequency of the electrical stimulation; and
responsive to determining the peak in the spectral power of the electrical signals at the second frequency, selecting, by the processing circuitry and based on the peak in the spectral power of the electrical signals, one electrode combination of the plurality of electrode combinations; and
controlling the medical device to deliver electrical stimulation therapy via the selected one electrode combination.

2. The method of claim 1, wherein:
controlling the medical device to deliver electrical stimulation comprises controlling the medical device to perform, for the plurality of electrode combinations, a respective sweep of a range of amplitude values; and
determining the peak in the spectral power comprises determining, for at least one electrode combination of the plurality of electrode combinations, the peak in the spectral power of the electrical signal at the second frequency for the respective electrode combination of the plurality of electrode combinations.

3. The method of claim 2, further comprising:
determining a time to perform the respective sweep of the range of amplitude values; and
controlling the medical device to deliver the electrical stimulation according to the sweep of the range of amplitude values at the determined time.

4. The method of claim 1, further comprising setting an upper amplitude bound at an amplitude value less than an amplitude of electrical stimulation that elicits the peak in the spectral power, the peak indicative of stimulation induced dyskinesia, wherein the upper amplitude bound limits amplitude of subsequent electrical stimulation delivered to the brain via the selected one electrode combination.

5. The method of claim 1, wherein the peak in a spectral power of the electrical signals is at one of a harmonic or a subharmonic frequency of the stimulation frequency.

6. The method of claim 1, wherein a magnitude of the peak in spectral power at the second frequency is an order of magnitude greater than the power at adjacent frequencies.

7. The method of claim 1, further comprising wherein selecting the one electrode combination comprises determining, by the processing circuitry and from the information representative of the electrical signals, that the one electrode combination sensed the electrical signals comprising the peak in the spectral power, and wherein the peak in the spectral power of the electrical signals sensed by the one electrode combination is greater in magnitude than any other peak in spectral power from other electrical signals of the plurality of electrical signals sensed by other electrode combinations of the plurality of electrode combinations.

8. The method of claim 7, further comprising delivering, by the medical device, the electrical stimulation to the brain of the patient via the one electrode combination.

9. The method of claim 7, wherein the one electrode combination is a first electrode combination, and wherein the method further comprises:
receiving subsequent information representative of respective electrical signals sensed by the first electrode combination and a second electrode combination different than the first electrode combination;
determining, from the information representative of the respective electrical signals, that the second electrode combination sensed a subsequent peak of spectral power having a greater magnitude than the peak of spectral power in the electrical signal sensed by the first electrode combination; and
controlling the medical device to deliver subsequent electrical stimulation via the second electrode combination instead of the first electrode combination.

10. The method of claim 1, further comprising determining, by the processing circuitry and based on the peak in spectral power, that the electrical simulation at the first frequency induced dyskinesia in the patient.

11. The method of claim 1, further comprising adjusting, by the processing circuitry and based on determination of the peak in spectral power, at least one therapy parameter that at least partially defines the electrical stimulation deliverable to the patient via the one electrode combination.

12. The method of claim 1, wherein the information comprises first information, and wherein the method further comprises:
receiving second information representative of a second electrical signal sensed by the one electrode combination;

determining, from the second information, an absence of a peak in a spectral power of the second electrical signal at the second frequency; and selecting a second electrode combination different than the first electrode combination for subsequent electrical stimulation.

13. The method of claim 1, further comprising outputting, for display, a representation of the peak in the spectral power of the electrical signal at the second frequency and an indication of the one electrode combination that sensed the electrical signal associated with the peak in the spectral power.

14. A system comprising:
processing circuitry configured to:
control a medical device to deliver electrical stimulation from a stimulation electrode combination and at a first frequency to a brain of a patient;
receive information representative of a plurality of electrical signals sensed by a plurality of electrode combinations and induced by the electrical stimulation delivered from the stimulation electrode combination, wherein each electrical signal of the plurality of electrical signals are sensed by a respective electrode combination of the plurality of electrode combinations;
determine, from the information representative of the plurality of electrical signals, a peak in a spectral power of the electrical signals at a second frequency lower than the first frequency of the electrical stimulation; and
responsive to determining the peak in the spectral power of the electrical signal at the second frequency, selecting, based on the peak in the spectral power of the electrical signal, one electrode combination of the plurality of electrode combinations; and
control the medical device to deliver electrical stimulation therapy via the selected one electrode combination.

15. The system of claim 14, wherein the processing circuitry is configured to:
control the medical device to deliver electrical stimulation by controlling the medical device to perform, for the plurality of electrode combinations, a respective sweep of a range of amplitude values; and
determine the peak in the spectral power by determining, for at least one electrode combination of the plurality of electrode combinations, the peak in the spectral power of the electrical signal at the second frequency for the respective electrode combination of the plurality of electrode combinations.

16. The system of claim 15, wherein the processing circuitry is further configured to:
determine a time to perform the respective sweep of the range of amplitude values; and
control the medical device to deliver the electrical stimulation according to the sweep of the range of amplitude values at the determined time.

17. The system of claim 14, wherein the processing circuitry is further configured to set an upper amplitude bound at an amplitude value less than an amplitude of electrical stimulation that elicits the peak in the spectral power, the peak indicative of stimulation induced dyskinesia, wherein the upper amplitude bound limits amplitude of subsequent electrical stimulation delivered to the brain via the selected one electrode combination.

18. The system of claim 14, wherein the peak in a spectral power of the electrical signals is at one of a harmonic or a subharmonic frequency of the stimulation frequency.

19. The system of claim 14, wherein a magnitude of the peak in spectral power at the second frequency is an order of magnitude greater than the power at adjacent frequencies.

20. The system of claim 14, wherein the processing circuitry is further configured to determine from the information representative of the electrical signals, that the one electrode combination sensed the electrical signals comprising the peak in the spectral power, and wherein the peak in the spectral power of the electrical signals sensed by the one electrode combination is greater in magnitude than any other peak in spectral power from other electrical signals of the plurality of electrical signals sensed by other electrode combinations of the plurality of electrode combinations.

21. The system of claim 20, further comprising stimulation circuitry configured to deliver the electrical stimulation to the brain of the patient via the one electrode combination.

22. The system of claim 20, wherein the electrode combination is a first electrode combination, and wherein the processing circuitry is configured to:
receive subsequent information representative of respective electrical signals sensed by the first electrode combination and a second electrode combination different than the first electrode combination;
determine, from the information representative of the respective electrical signals, that the second electrode combination sensed a subsequent peak of spectral power having a greater magnitude than the peak of spectral power in the electrical signal sensed by the first electrode combination; and
control the medical device to deliver subsequent electrical stimulation via the second electrode combination instead of the first electrode combination.

23. The system of claim 14, wherein the processing circuitry is further configured to determine, based on the peak in spectral power, that the electrical simulation at the first frequency induced dyskinesia in the patient.

24. The system of claim 14, wherein the processing circuitry is further configured to adjust, based on determination of the peak in spectral power, at least one therapy parameter that at least partially defines the electrical stimulation deliverable to the patient via the one electrode combination.

25. The system of claim 14, wherein the information comprises first information, and wherein the processing circuitry is further configured to:
receive second information representative of a second electrical signal sensed by the one electrode combination;
determine, from the second information, an absence of a peak in a spectral power of the second electrical signal at the second frequency; and
select a second electrode combination different than the first electrode combination for subsequent electrical stimulation.

26. The system of claim 14, wherein the processing circuitry is configured to output, for display, a representation of the peak in the spectral power of the electrical signal at the second frequency and an indication of the one electrode combination that sensed the electrical signal associated with the peak in the spectral power.

27. A non-transitory computer readable medium comprising instructions that, when executed, cause processing circuitry to:

control a medical device to deliver electrical stimulation from a stimulation electrode combination and at a first frequency to a brain of a patient;

receive information representative of a plurality of electrical signals sensed by a plurality of electrode combinations and induced by the electrical stimulation delivered from the stimulation electrode combination, wherein each electrical signal of the plurality of electrical signals are sensed by a respective electrode combination of the plurality of electrode combinations;

determine from the information representative of the plurality of electrical signals, a peak in a spectral power of the electrical signals at a second frequency lower than the first frequency of the electrical stimulation;

determine based on the peak in spectral power, that the electrical simulation induced dyskinesia in the patient;

determine from the information representative of the electrical signals, one electrode combination that sensed the peak in the spectral power, and wherein the peak in the spectral power sensed by the one electrode combination is greater in magnitude than any other peak in spectral power from an electrical signal of the electrical signals sensed by other electrode combinations of the plurality of electrode combinations;

adjust based on determination of the peak in spectral power, at least one therapy parameter that at least partially defines subsequent electrical stimulation deliverable to the patient; and control the medical device to deliver the subsequent electrical stimulation via the one electrode combination and according to the adjusted at least one therapy parameter.

* * * * *